(12) United States Patent
Tada et al.

(10) Patent No.: US 11,818,950 B2
(45) Date of Patent: Nov. 14, 2023

(54) ORGANIC ELECTROLUMINESCENCE ELEMENT

(71) Applicant: NIPPON STEEL & SUMIKIN CHEMICAL CO., LTD., Tokyo (JP)

(72) Inventors: Masashi Tada, Tokyo (JP); Kazuaki Yoshimura, Tokyo (JP); Atsushi Kawada, Tokyo (JP); Katsuhide Noguchi, Tokyo (JP); Yuta Sagara, Tokyo (JP); Junya Ogawa, Tokyo (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 400 days.

(21) Appl. No.: 16/063,156

(22) PCT Filed: Nov. 28, 2016

(86) PCT No.: PCT/JP2016/085114
§ 371 (c)(1),
(2) Date: Jun. 15, 2018

(87) PCT Pub. No.: WO2017/115596
PCT Pub. Date: Jul. 6, 2017

(65) Prior Publication Data
US 2018/0366656 A1 Dec. 20, 2018

(30) Foreign Application Priority Data
Dec. 28, 2015 (JP) ................................. 2015-257094

(51) Int. Cl.
*C07D 487/04* (2006.01)
*C09K 11/06* (2006.01)
*C07D 519/00* (2006.01)
*H10K 50/11* (2023.01)
*H10K 101/00* (2023.01)
*H10K 85/60* (2023.01)

(52) U.S. Cl.
CPC ....... *H10K 85/6572* (2023.02); *C07D 487/04* (2013.01); *C07D 519/00* (2013.01); *C09K 11/06* (2013.01); *C09K 2211/1018* (2013.01); *H10K 50/11* (2023.02); *H10K 2101/90* (2023.02)

(58) Field of Classification Search
None
See application file for complete search history.

(56) References Cited

U.S. PATENT DOCUMENTS

| 2006/0103298 | A1* | 5/2006 | Lee | 313/504 |
| 2006/0134460 | A1* | 6/2006 | Kondakova | 428/690 |
| 2007/0252516 | A1* | 11/2007 | Kondakova | 313/504 |
| 2009/0030202 | A1* | 1/2009 | Iwakuma | 544/251 |
| 2009/0072727 | A1 | 3/2009 | Takeda | |
| 2010/0295444 | A1 | 11/2010 | Kuma et al. | |
| 2012/0241732 | A1 | 9/2012 | Endo et al. | |
| 2012/0305903 | A1* | 12/2012 | Kai | 257/40 |
| 2013/0075716 | A1* | 3/2013 | Nishimura | 257/40 |
| 2013/0248845 | A1 | 9/2013 | Ogawa et al. | |
| 2014/0131686 | A1 | 5/2014 | Kawakami et al. | |
| 2015/0053958 | A1* | 2/2015 | Ishisone | H01L 51/5016 257/40 |
| 2015/0105564 | A1 | 4/2015 | Adachi et al. | |
| 2015/0126736 | A1* | 5/2015 | Cho | H01L 51/0067 |
| 2015/0129849 | A1 | 5/2015 | Kwong et al. | |
| 2017/0186974 | A1* | 6/2017 | Jung | H01L 51/0072 |
| 2018/0170914 | A1 | 6/2018 | Miyata et al. | |

FOREIGN PATENT DOCUMENTS

| CN | 107531628 A | 1/2018 |
| EP | 3 015 457 A1 | 5/2016 |
| JP | 2015-106659 A | 6/2015 |
| JP | 2015-109428 A | 6/2015 |

OTHER PUBLICATIONS

Deaton et al. "The blue aluminum and gallium chelates for OLEDs" Inorganica Chimica Acta, 2008, vol. 361, p. 1020-1035, Jul. 18, 2007 (Year: 2007).*
The First Office Action for the Application No. 201680076418.8 from The State Intellectual Property Office of the People's Republic of China dated Aug. 19, 2019.
English Translation of the International Preliminary Report on Patentability (PCT/IPEA/409) for the Application No. PCT/JP2016/085114 dated Jun. 28, 2018.
International Search Report for the Application No. PCT/JP2016/085114 dated Feb. 28, 2017.
Uoyama, Hiroki et al., "Highly efficient organic light-emitting diodes from delayed fluorescence", Nature, 2012, vol. 492, pp. 234-238.

* cited by examiner

*Primary Examiner* — Dylan C Kershner
*Assistant Examiner* — Seokmin Jeon
(74) *Attorney, Agent, or Firm* — Birch, Stewart, Kolasch & Birch, LLP

(57) ABSTRACT

Provided is a thermally activated delayed fluorescent organic electroluminescent device having a low driving voltage, high luminous efficiency, and a long lifetime. The organic electroluminescent device includes light-emitting layers between an anode and a cathode opposite to each other, and at least one of the light-emitting layers contains a thermally activated delayed fluorescent material, or the thermally activated delayed fluorescent material and a host material. The thermally activated delayed fluorescent material is represented by the following general formula (1) where A represents an electron-withdrawing group, such as a CN group, and $D^1$ and $D^2$ each represent an electron-donating group having an indole ring structure.

9 Claims, 5 Drawing Sheets

ORGANIC ELECTROLUMINESCENCE ELEMENT

TECHNICAL FIELD

The present invention relates to an organic electroluminescent device (referred to as "organic EL device").

BACKGROUND ART

When a voltage is applied to an organic EL device, a hole is injected from an anode into a light-emitting layer, and an electron is injected from a cathode into the layer. Then, in the light-emitting layer, the hole and the electron thus injected recombine to produce an exciton. At this time, according to the statistical law of electron spins, singlet excitons and triplet excitons are produced at a ratio of 1:3. The internal quantum efficiency of a fluorescent emission-type organic EL device using light emission by a singlet exciton is said to be at most 25%. Meanwhile, it has been known that the internal quantum efficiency of a phosphorescent emission-type organic EL device using light emission by a triplet exciton can be improved to 100% when intersystem crossing from a singlet exciton is efficiently performed.

In recent years, a technology for the lengthening of the lifetime of a phosphorescent organic EL device has been advancing, and has started to be applied to the display of a cellular phone or the like. With regard to a blue organic EL device, however, a practical phosphorescent emission-type organic EL device has not been developed, and hence the development of a blue organic EL device having high efficiency and a long lifetime has been required.

Further, a high-efficiency organic EL device utilizing delayed fluorescence has been recently developed. In, for example, Patent Literature 1, there is a disclosure of an organic EL device utilizing a triplet-triplet fusion (TTF) mechanism serving as one of the delayed fluorescence mechanisms. The TTF mechanism utilizes a phenomenon in which a singlet exciton is produced by collision between two triplet excitons, and is considered to be capable of improving internal quantum efficiency to 40% in theory. However, a further improvement in efficiency has been required because the efficiency of the device is lower than that of a phosphorescent light-emitting organic EL device.

Meanwhile, in Patent Literature 2, there is a disclosure of an organic EL device utilizing a thermally activated delayed fluorescence (TADF) mechanism. The TADF mechanism utilizes a phenomenon in which inverse intersystem crossing from a triplet exciton to a singlet exciton occurs in a material having a small energy difference between a singlet level and a triplet level, and is considered to be capable of improving internal quantum efficiency to 100% in theory. However, a further improvement in lifetime characteristic has been required as in a phosphorescent light-emitting device.

CITATION LIST

Patent Literature

[PTL 1] WO 2010/134350 A1
[PTL 2] WO 2011/070963 A1
[PTL 3] WO 2013/154064 A1
[PTL 4] WO 2014/208698 A1
[PTL 5] JP 2015-106659 A
[PTL 6] JP 2015-109428 A

Non Patent Literature

[NPL 1] Nature, 2012, 492, 234

In Patent Literature 2, there is a disclosure of the use of such an indolocarbazole compound as shown below as a TADF material.

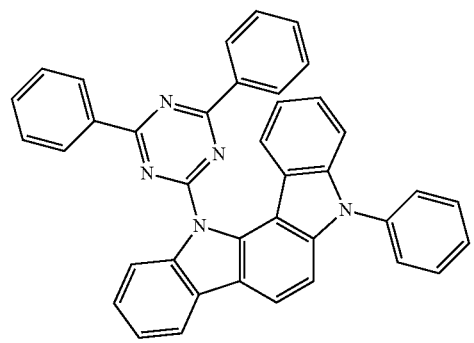 [SMILES: c1ccc(-c2nc(-c3ccccc3)nc(-n3c4ccccc4c4ccc5c(c6ccccc6n5-c5ccccc5)c43)n2)cc1]

In Non Patent Literature 1, there is a disclosure of the use of a cyanobenzene compound substituted with carbazole as a TADF material.

In Patent Literature 3, there is a disclosure of the use of a cyanobenzene compound substituted with carbazole or indole as a TADF material.

In each of Patent Literatures 4, 5, and 6, there is a disclosure of the use of a cyanobenzene compound substituted with such indolocarbazole as shown below as a TADF material.

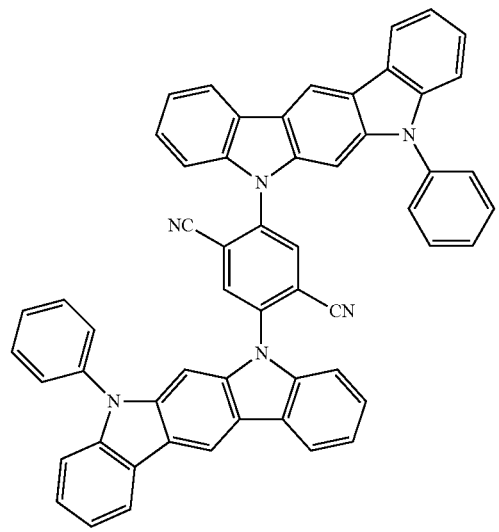 [SMILES: N#Cc1cc(-n2c3ccccc3c3cc4c5ccccc5n(-c5ccccc5)c4cc32)c(C#N)cc1-n1c2ccccc2c2cc3c4ccccc4n(-c4ccccc4)c3cc21]

However, each of the literatures cannot be said to be sufficient, and hence a further improvement has been desired.

SUMMARY OF INVENTION

In order to apply an organic EL device to a display device, such as a flat panel display, or a light source, the luminous efficiency of the device needs to be improved, and at the same time, stability at the time of its driving needs to be sufficiently secured. In view of the above-mentioned present circumstances, an object of the present invention is to provide a practically useful organic EL device having high efficiency and high driving stability while having a low driving voltage.

According to one embodiment of the present invention, there is provided an organic EL device, including one or more light-emitting layers between an anode and a cathode opposite to each other, wherein at least one of the light-emitting layers contains a thermally activated delayed fluorescent material represented by the following general formula (1):

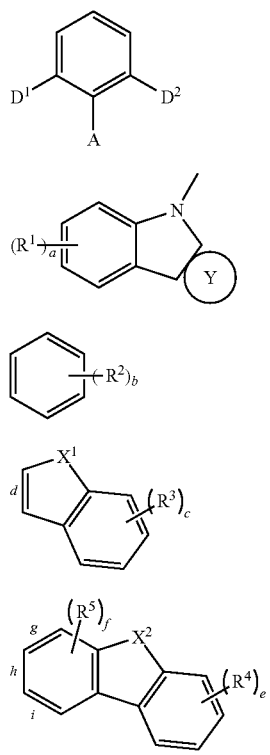

where $D^1$ and $D^2$ each represent a nitrogen-containing heterocycle represented by the formula (1a), a ring Y in the formula (1a) is a ring structure represented by the formula (1a-1), (1a-2), or (1a-3), and when the ring Y is represented by the formula (1a-2), the ring Y is fused at a position d, and when the ring Y is represented by the formula (1a-3), the ring Y is fused at any one of positions g, h, and i, $X^1$ and $X^2$ each independently represent O, S, or N—$R^6$, $R^1$ to $R^6$ each independently represent an aliphatic hydrocarbon group having 1 to 8 carbon atoms, an aromatic hydrocarbon group having 6 to 10 carbon atoms, or an aromatic heterocyclic group having 3 to 12 carbon atoms, A represents a cyano group, a nitro group, a trifluoromethyl group, chlorine, or fluorine, a, b, c, and e each independently represent an integer of from 0 to 4, and f represents an integer of from 0 to 2.

In the general formula (1), A preferably represents a cyano group, the ring Y is preferably represented by the formula (1a-2) or (1a-3), and is more preferably represented by the formula (1a-3), $X^2$ in the formula (1a-3) preferably represents $NR^6$, and $R^6$ has the same meaning as that in the formula (1a-3).

In the organic EL device of the present invention, the light-emitting layer containing the thermally activated delayed fluorescent material represented by the general formula (1) may contain a host material.

As the host material, there is given a compound represented by the following general formula (2):

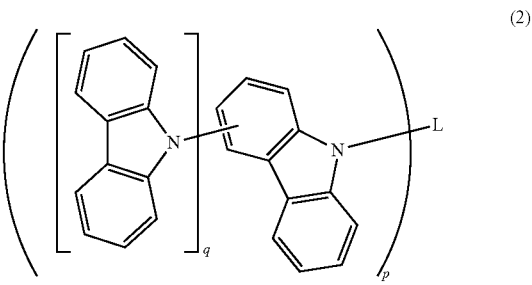

where L represents a p-valent group produced from benzene, dibenzofuran, dibenzothiophene, carborane, or a compound obtained by linking two or three of the rings, p represents an integer of 1 or 2, and q represents an integer of from 0 to 4, provided that when L represents a p-valent group produced from benzene, q represents an integer of from 1 to 4.

It is preferred that the light-emitting layer contain, as the host material, a first host and a second host selected from compounds each having a singlet excitation energy (S1) larger than that of the first host. In addition, it is preferred that at least one of the first host or the second host include a compound represented by the general formula (2), and it is more preferred that both the first host and the second host include compounds each represented by the general formula (2).

It is preferred that an ionization potential (IP) of the thermally activated delayed fluorescent material represented by the general formula (1) in the light-emitting layer be smaller than an IP of the host material.

It is preferred that in the organic EL device, an emission wavelength of the thermally activated delayed fluorescent material represented by the general formula (1) have an emission maximum wavelength in a range of from 440 nm to 470 nm.

The organic EL device of the present invention can be an organic EL device having a low driving voltage, high luminous efficiency, and a long lifetime because the device contains a specific thermally activated delayed fluorescent material and a specific host material in a light-emitting layer thereof.

DESCRIPTION OF EMBODIMENTS

Figure 1:
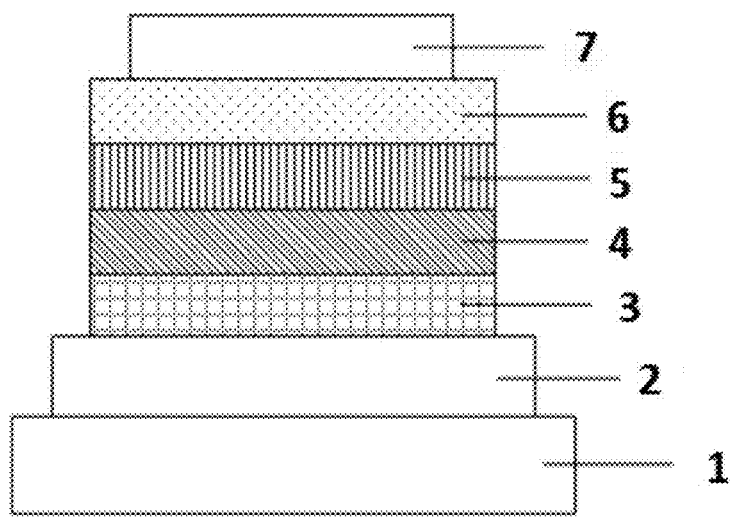
FIG. 1 is a schematic sectional view for illustrating an example of an organic EL device.

An organic EL device of the present invention includes one or more light-emitting layers between an anode and a cathode opposite to each other, and at least one of the light-emitting layers contains a thermally activated delayed fluorescent material (referred to as "TADF material") represented by the general formula (1). The organic EL device has an organic layer formed of a plurality of layers between the anode and the cathode opposite to each other, and at least one of the plurality of layers is a light-emitting layer. A host material can be incorporated into the light-emitting layer as required, and a preferred host material is a compound represented by the general formula (2).

The general formula (1) is described.

Substituents $D^1$ and $D^2$ are each a nitrogen-containing heterocycle represented by the formula (1a), and $D^1$ and $D^2$ may be identical to or different from each other.

A ring Y in the formula (1a) is a ring structure represented by the formula (1a-1), (1a-2), or (1a-3), d, g, h, and i each represent a side on which the ring Y is fused with an adjacent pyrrole ring. When the ring Y is represented by the formula (1a-2), the ring Y is fused at the position d, and when the ring Y is represented by the formula (1a-3), the ring Y is fused at any one of the positions g, h, and i. When the ring Y is represented by the formula (1a-1), the ring Y is fused at any position of the benzene ring.

The ring Y in the formula (1a) of at least one of $D^1$ or $D^2$ is preferably a ring structure represented by the formula (1a-2) or the formula (1a-3). The ring Y is more preferably a ring structure represented by the formula (1a-3), still more preferably a ring structure represented by the formula (1a-3) in which $X^2$ represents N—$R^6$.

In the formula (1a-2) or (1a-3), $X^1$ and $X^2$ each independently represent O, S, or N—$R^6$.

In the formulae (1a), (1a-1), (1a-2), and (1a-3), $R^1$ to $R^6$ each independently represent an aliphatic hydrocarbon group having 1 to 8 carbon atoms, an aromatic hydrocarbon group having 6 to 10 carbon atoms, or an aromatic heterocyclic group having 3 to 12 carbon atoms, preferably each independently represent an aliphatic hydrocarbon group having 1 to 6 carbon atoms, an aromatic hydrocarbon group having 6 to 8 carbon atoms, or an aromatic heterocyclic group having 3 to 9 carbon atoms, and more preferably each independently represent a phenyl group or an aromatic heterocyclic group having 3 to 6 carbon atoms.

a, b, c, and e each independently represent an integer of from 0 to 4, preferably an integer of from 0 to 2, more preferably an integer of 0 or 1. f represents an integer of from 0 to 2, preferably an integer of 0 or 1.

Specific examples of the aliphatic hydrocarbon group having 1 to 8 carbon atoms include methyl, ethyl, propyl, butyl, pentyl, hexyl, heptyl, and octyl.

Specific examples of the aromatic hydrocarbon group having 6 to 10 carbon atoms or the aromatic heterocyclic group having 3 to 12 carbon atoms include aromatic groups each produced by removing one H atom from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, dibenzofuran, dibenzothiophene, dibenzoselenophene, or carbazole. Preferred example thereof include aromatic groups each produced from benzene, pyridine, pyrimidine, triazine, thiophene, isothiazole, thiazole, pyridazine, pyrrole, pyrazole, imida-zole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzoisothiazole, or benzothiadiazole. More preferred examples thereof include aromatic groups each produced from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, or oxadiazole.

A represents a cyano group, a nitro group, a trifluoromethyl group, chlorine, or fluorine, preferably a cyano group, a nitro group, or a trifluoromethyl group, more preferably a cyano group.

Specific examples of the compound represented by the general formula (1) are shown below. However, the compound is not limited to these exemplified compounds.

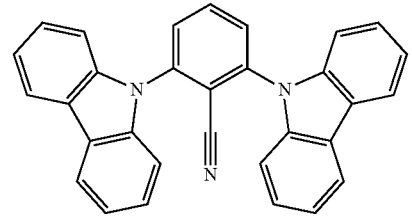

1-1

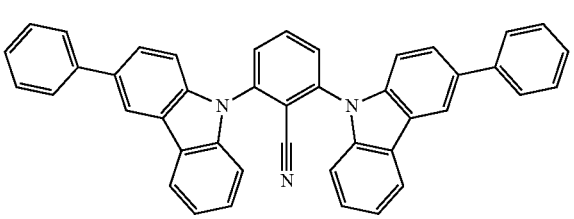

1-2

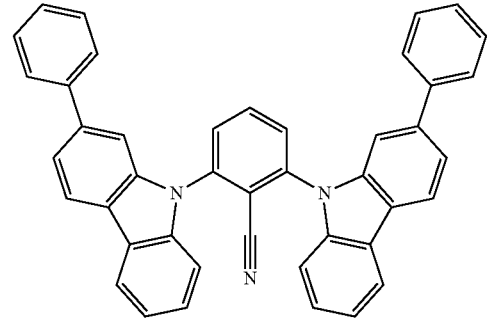

1-3

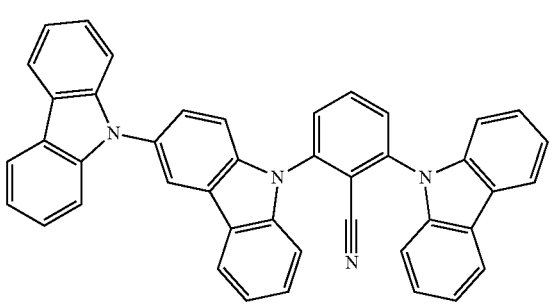

1-4

1-5
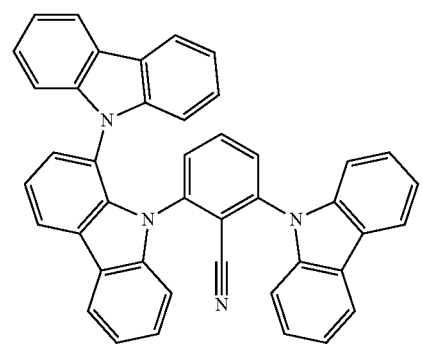
1-6
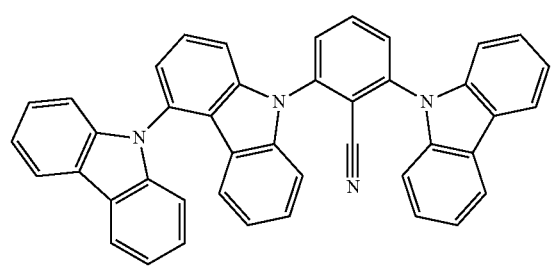
1-7
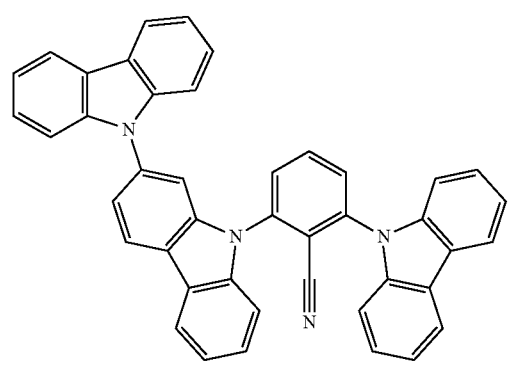
1-8
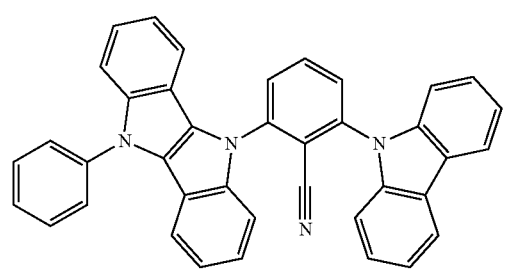
1-9
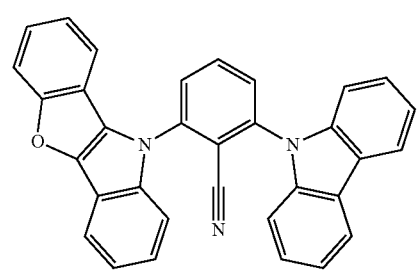
1-10
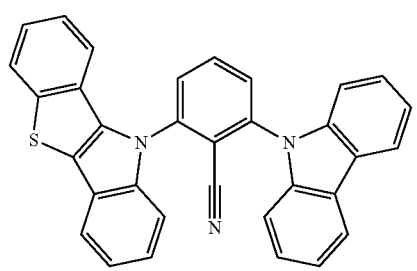
1-11
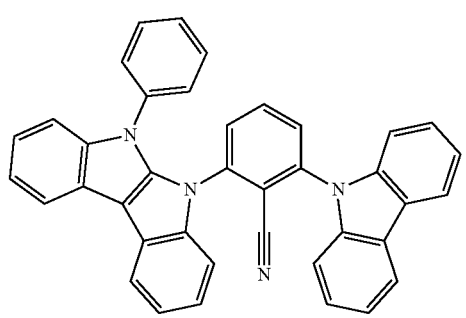
1-12
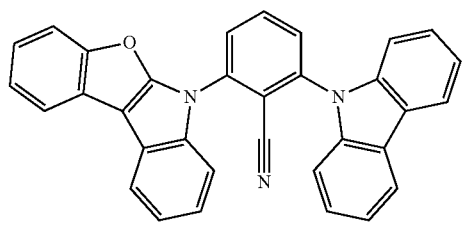
1-13
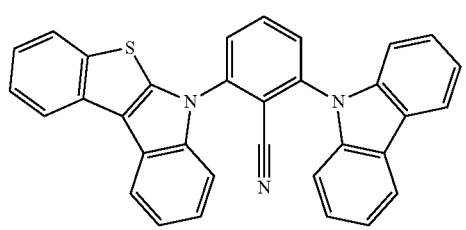
1-14
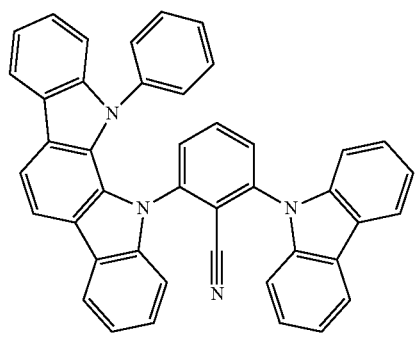

1-15
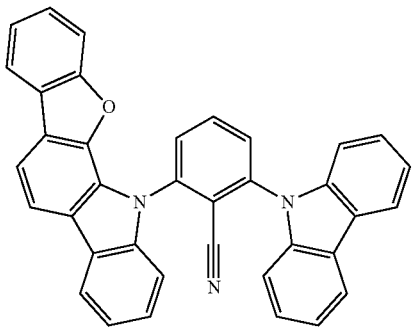
1-16
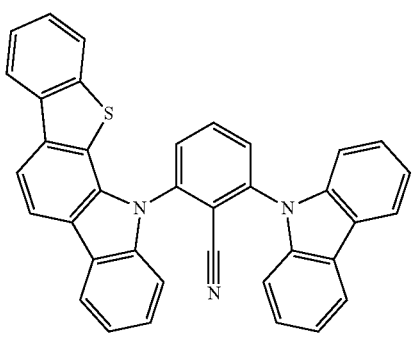
1-17
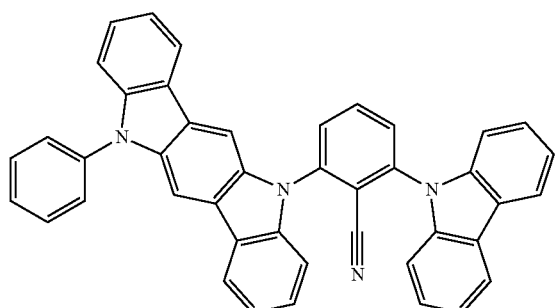
1-18
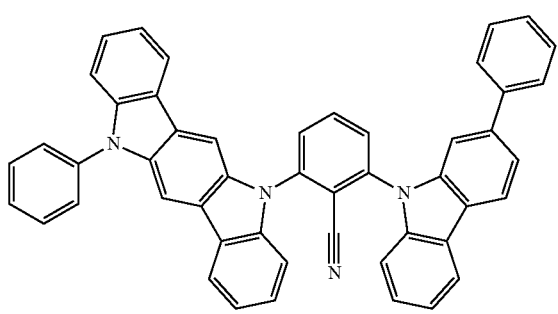
1-19
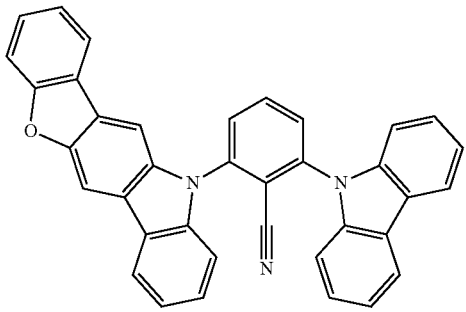
1-20
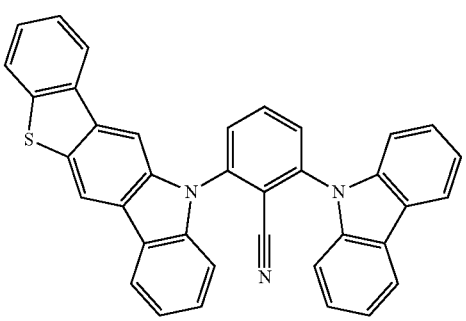
1-21
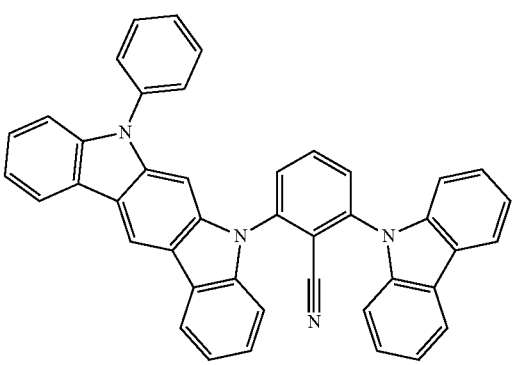
1-22
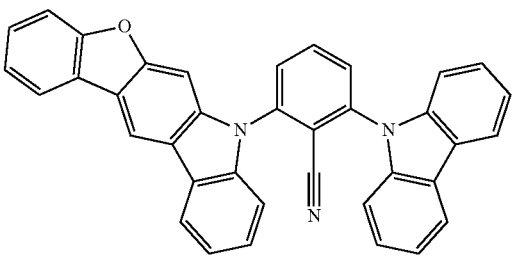
1-23
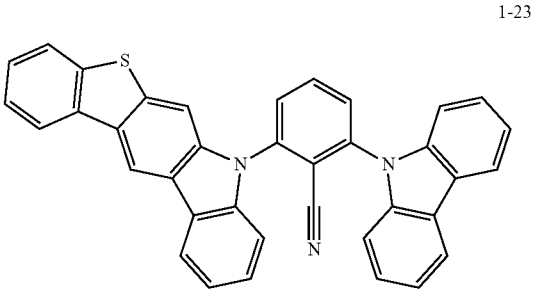
1-24
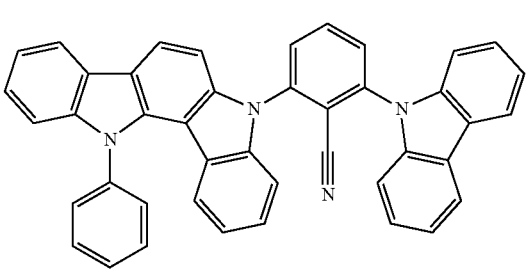

-continued
1-25
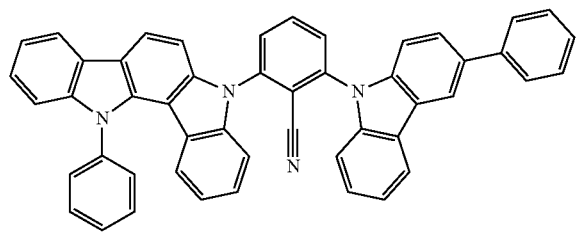
1-26
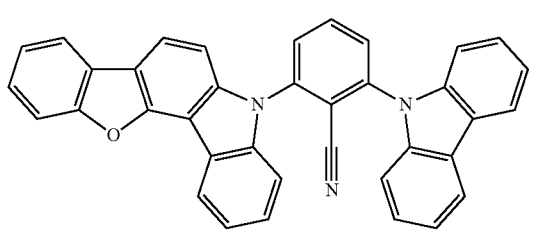
1-27
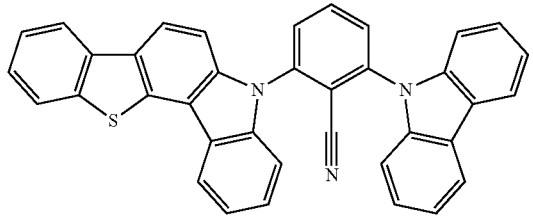
1-28
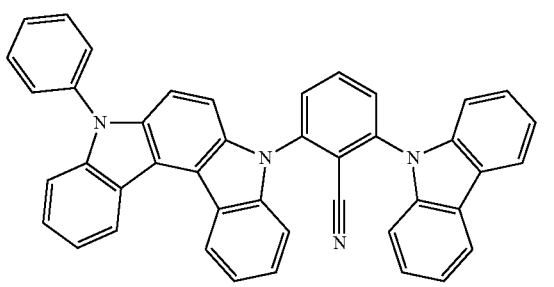
1-29
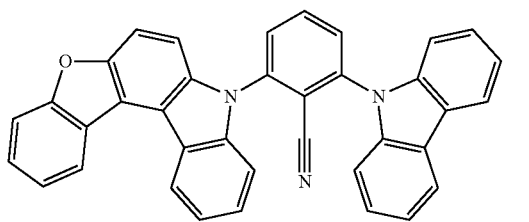
1-30
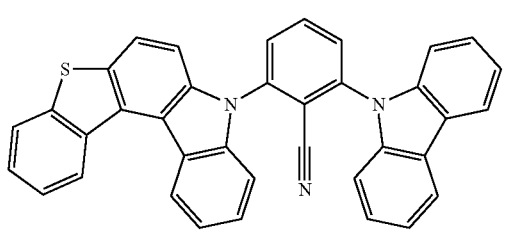
-continued
1-31
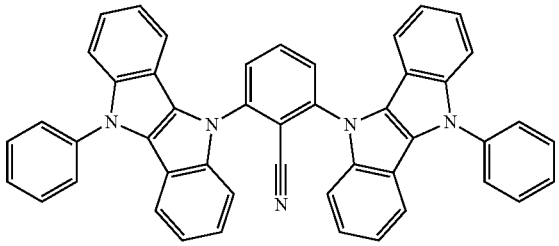
1-32
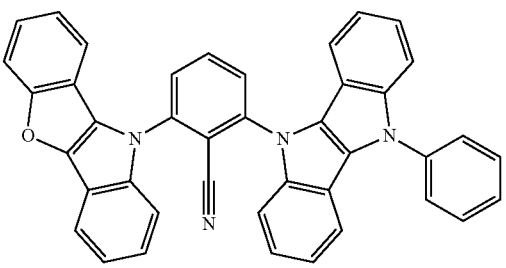
1-33
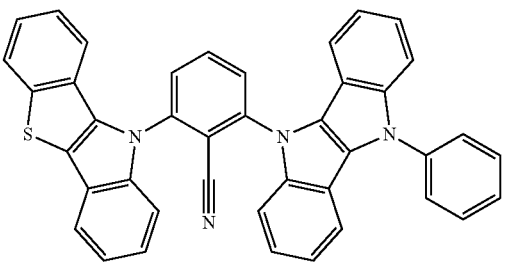
1-34
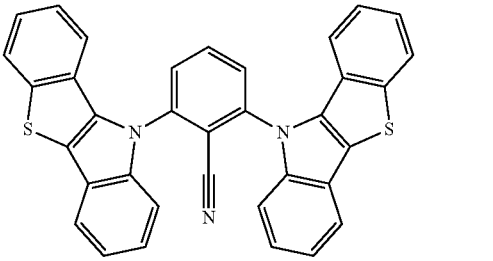
1-35
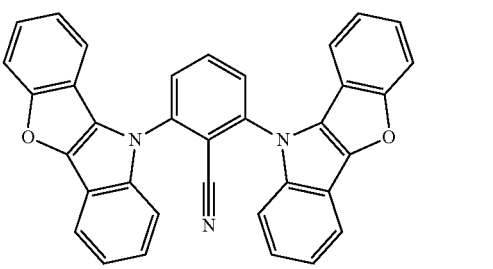
1-36
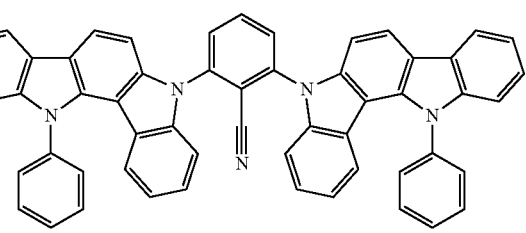

1-37
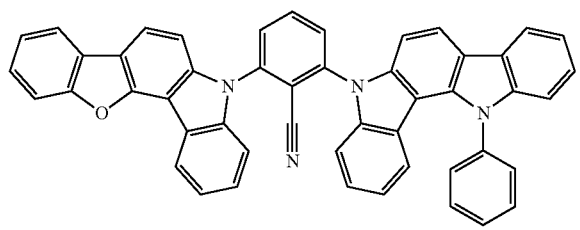
1-38
1-43
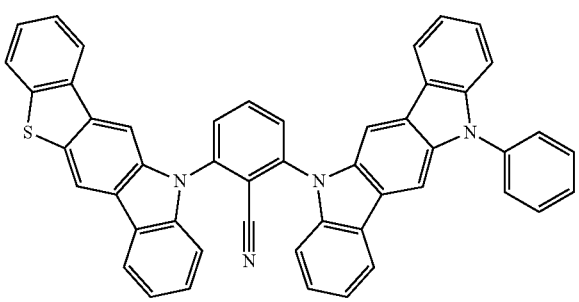
1-39
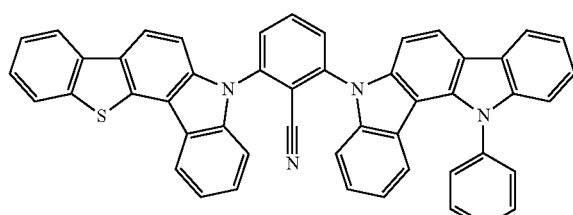
1-40
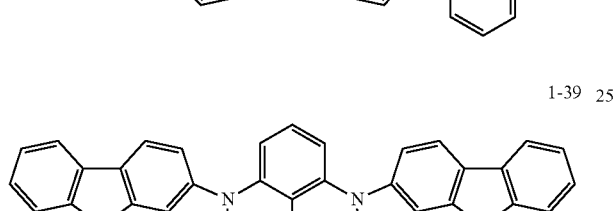
1-44
1-41
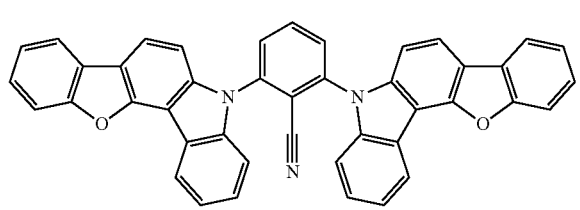
1-45
1-42
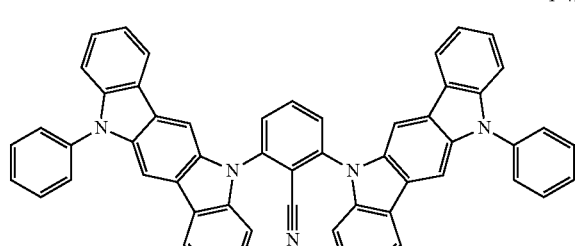
1-46
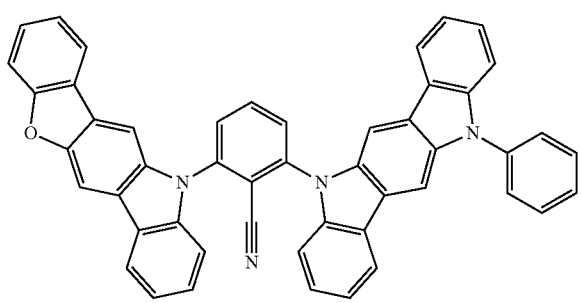

-continued
1-47
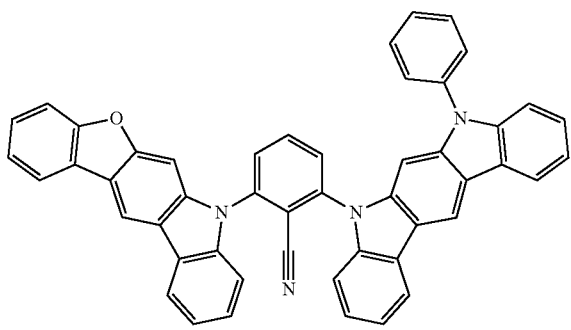
1-52
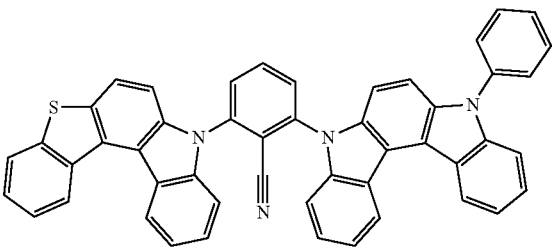
1-48
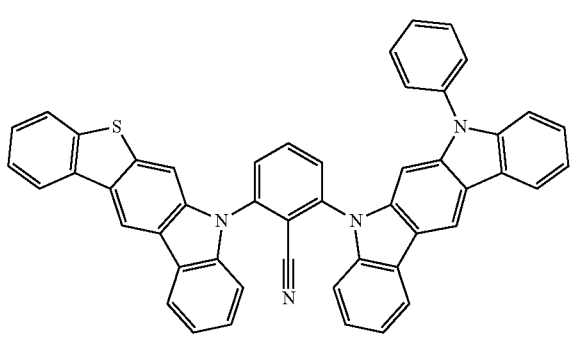
1-53
1-49
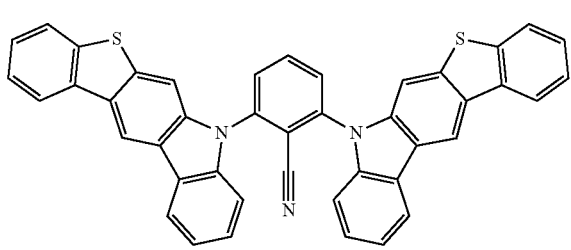
1-54
1-50
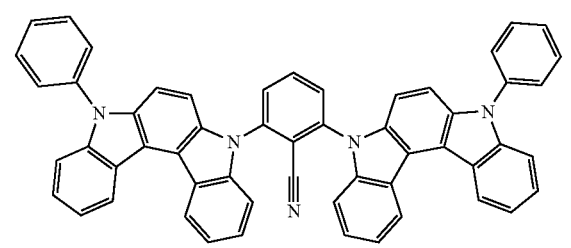
1-55
1-51
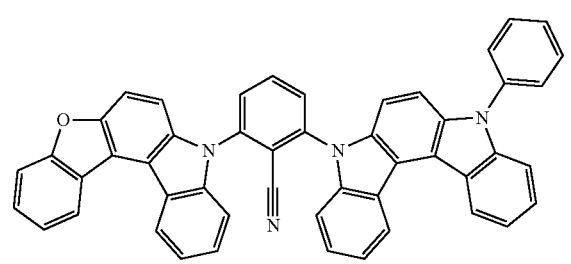
1-56
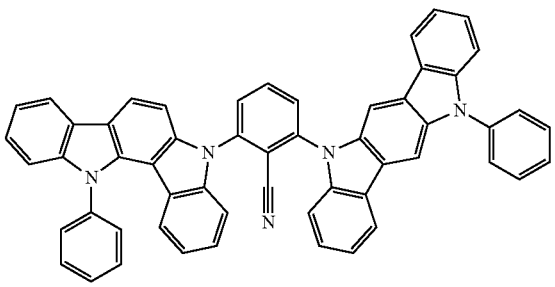

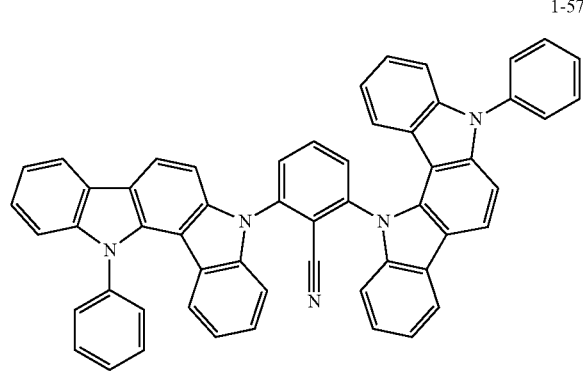

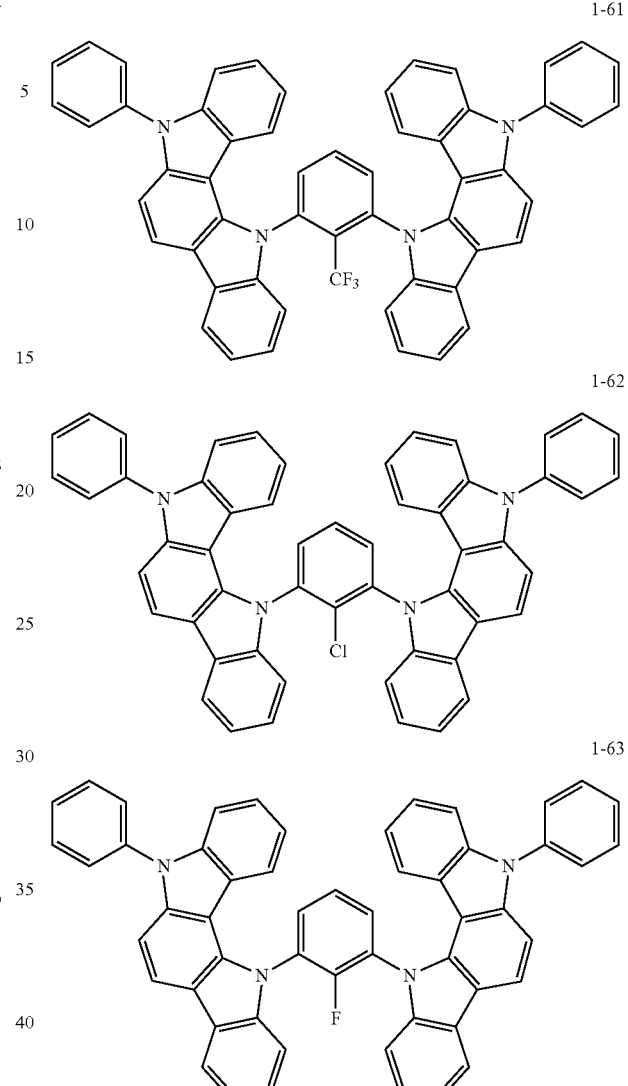

An excellent organic EL device can be obtained by incorporating a compound represented by the general formula (1) as a TADF material into a light-emitting layer.

In addition, a host material can be incorporated into the light-emitting layer together with the TADF material as required. The incorporation of the host material provides an excellent organic EL device. In this case, the TADF material is also referred to as "dopant". The host material accelerates the emission of light from the TADF material serving as the dopant. The host material desirably has an ionization potential (IP) larger than that of the TADF material. In addition, the host material desirably has a singlet excitation energy (S1) larger than that of the TADF material.

A compound represented by the general formula (2) is suitable as the host material.

In the general formula (2), L represents a p-valent group, and represents a p-valent group produced from benzene, dibenzofuran, dibenzothiophene, carborane, or a linked compound obtained by linking two or three of the rings. Here, the linked compound is a compound having a structure in which benzene, dibenzofuran, dibenzothiophene, or carborane rings are linked to each other by direct bonding, and is represented by Ar—Ar, Ar—Ar—Ar, or Ar—Ar(Ar). Here, Ar represents a benzene, dibenzofuran, dibenzothiophene, or carborane ring, and a plurality of Ar's may be identical to or different from each other. A preferred linked compound is, for example, biphenyl or terphenyl serving as a compound in which two or three benzene rings are linked to each other.

L preferably represents a p-valent group produced by removing p hydrogen atoms from benzene, biphenyl, terphenyl, dibenzofuran, dibenzothiophene, or carborane. p represents an integer of 1 or 2, and preferably represents an integer of 1. q represents an integer of from 0 to 4, preferably represents an integer of from 0 to 3, and more preferably represents an integer of from 0 to 2. However, when L represents a group produced from benzene, q does not represent 0.

In the general formula (2), L and a carbazole ring may each have a substituent as long as a function as a host is not inhibited. Such substituent is, for example, a hydrocarbon group having 1 to 8 carbon atoms or an alkoxy group having 1 to 8 carbon atoms, and is preferably an alkyl group having 1 to 3 carbon atoms or an alkoxy group having 1 to 3 carbon atoms. The number of the substituents is preferably from 0 to 4.

Specific examples of the compound represented by the general formula (2) are shown below.

2-1

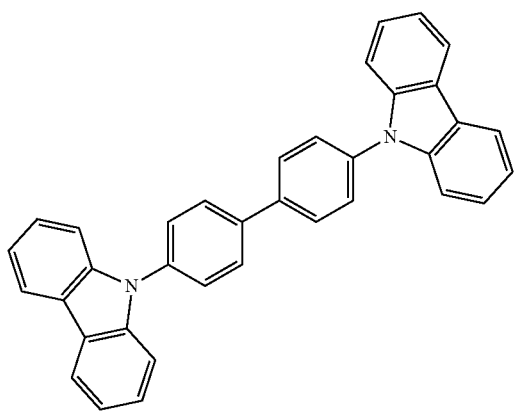

2-2

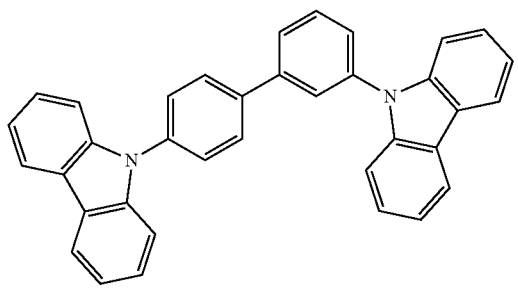

2-3

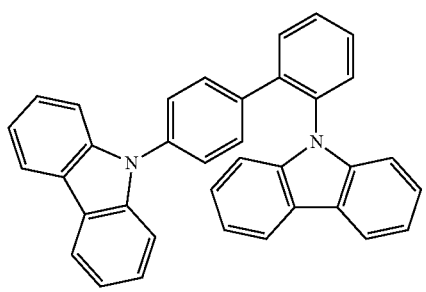

2-4

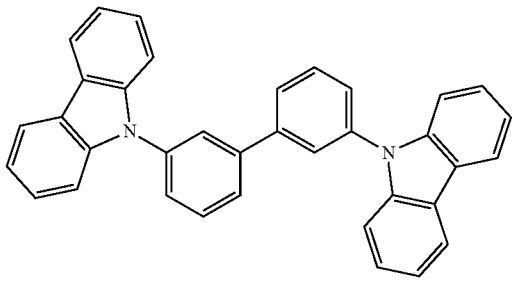

2-5

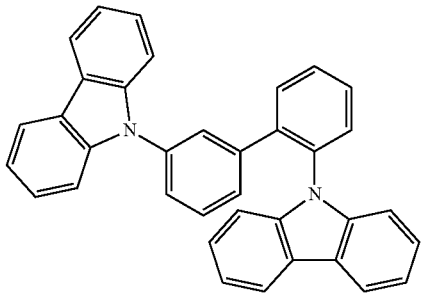

2-6

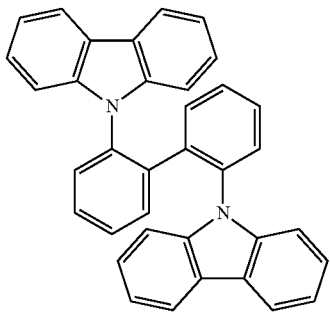

2-7

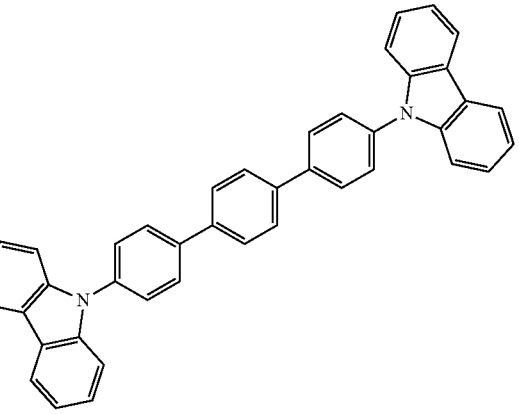

2-8

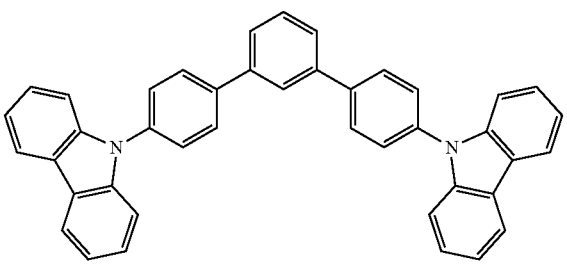

-continued
2-9
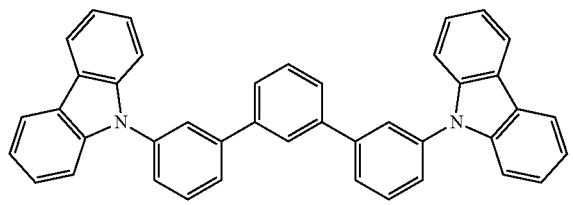
2-10
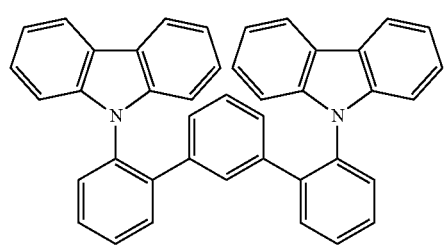
2-11
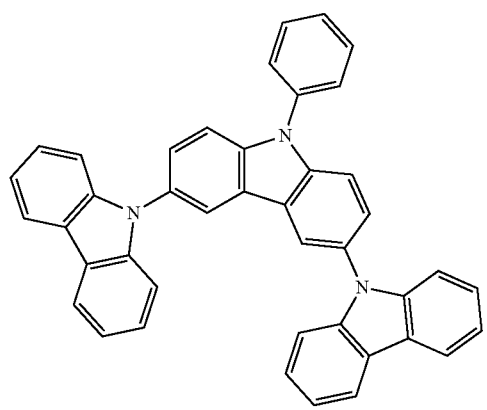
2-12
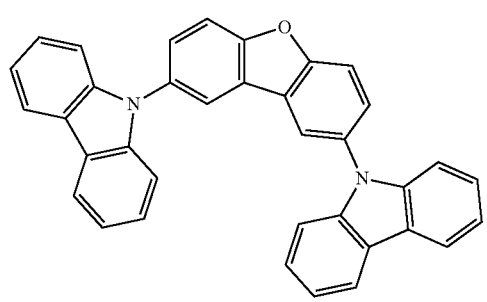
2-13
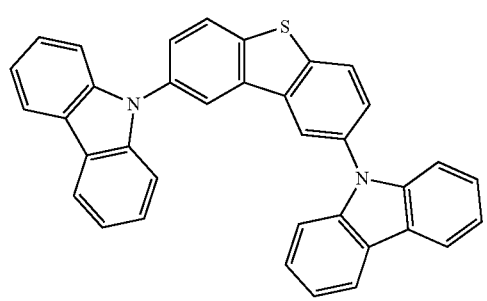
-continued
2-14
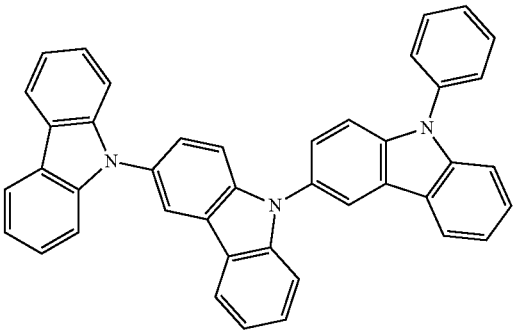
2-15
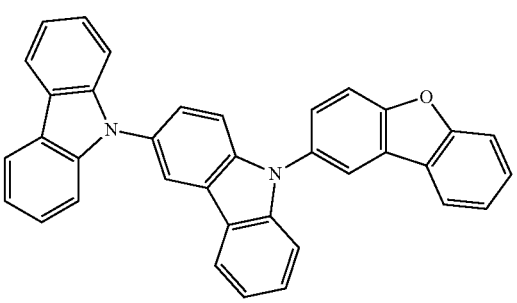
2-16
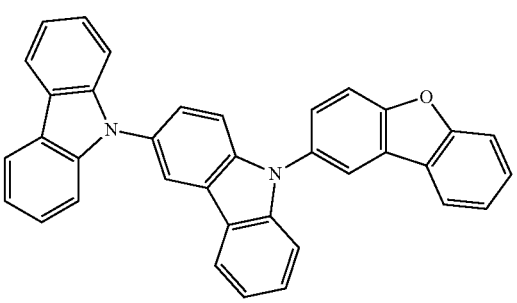
2-17
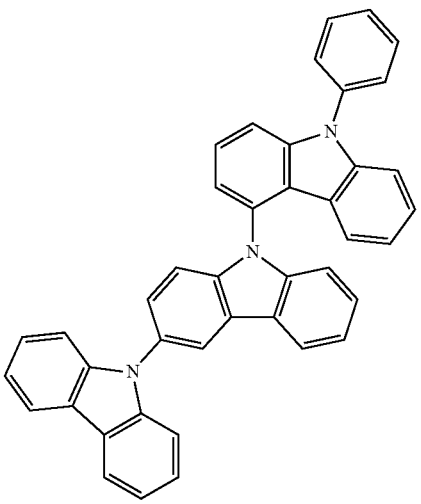

2-18
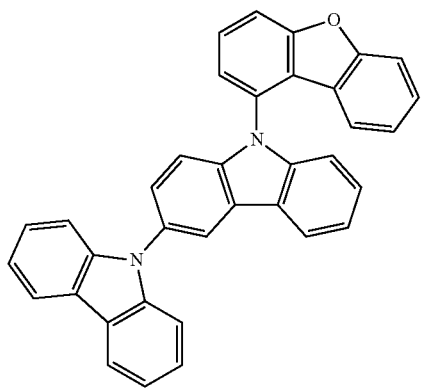
2-19
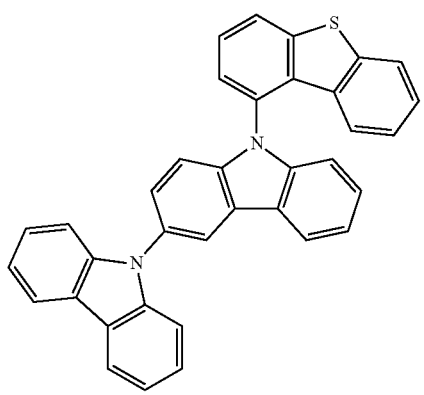
2-20
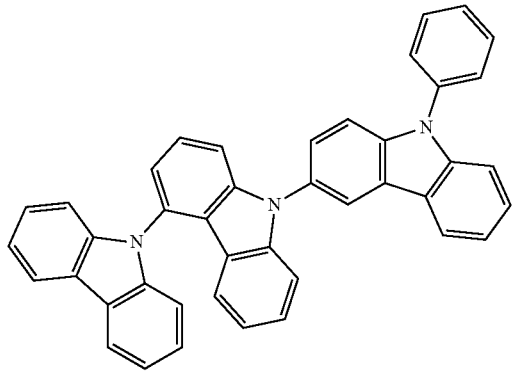
2-21
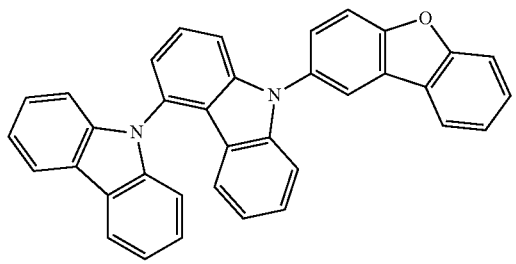
2-22
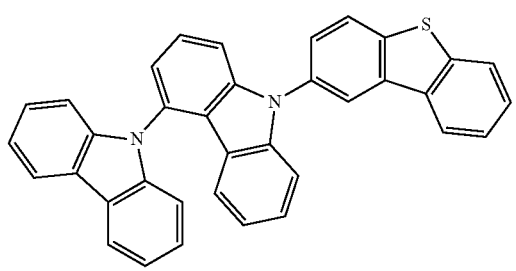
2-23
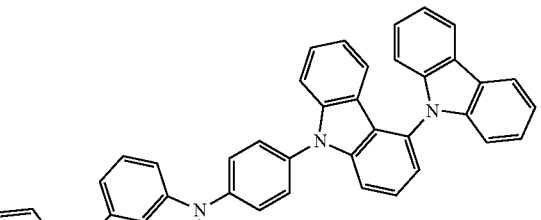
2-24
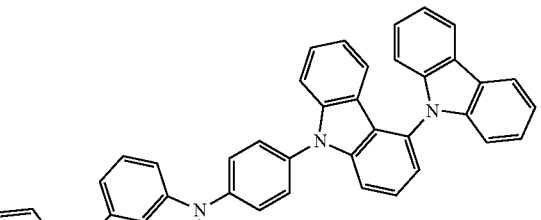
2-25
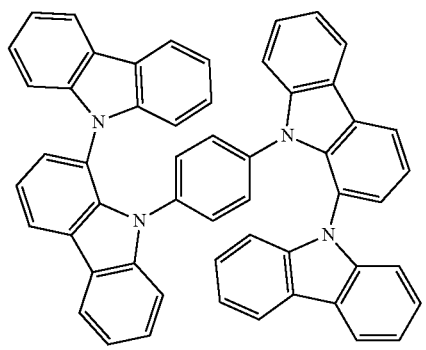

-continued
2-26
2-27
2-28
2-29
2-30
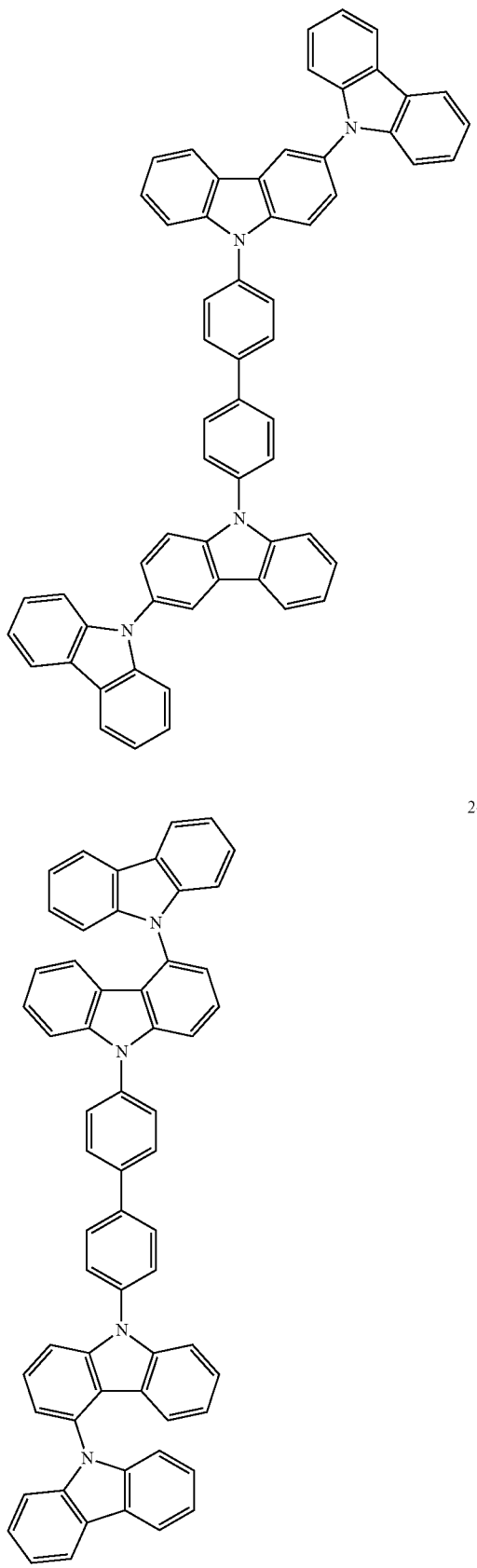
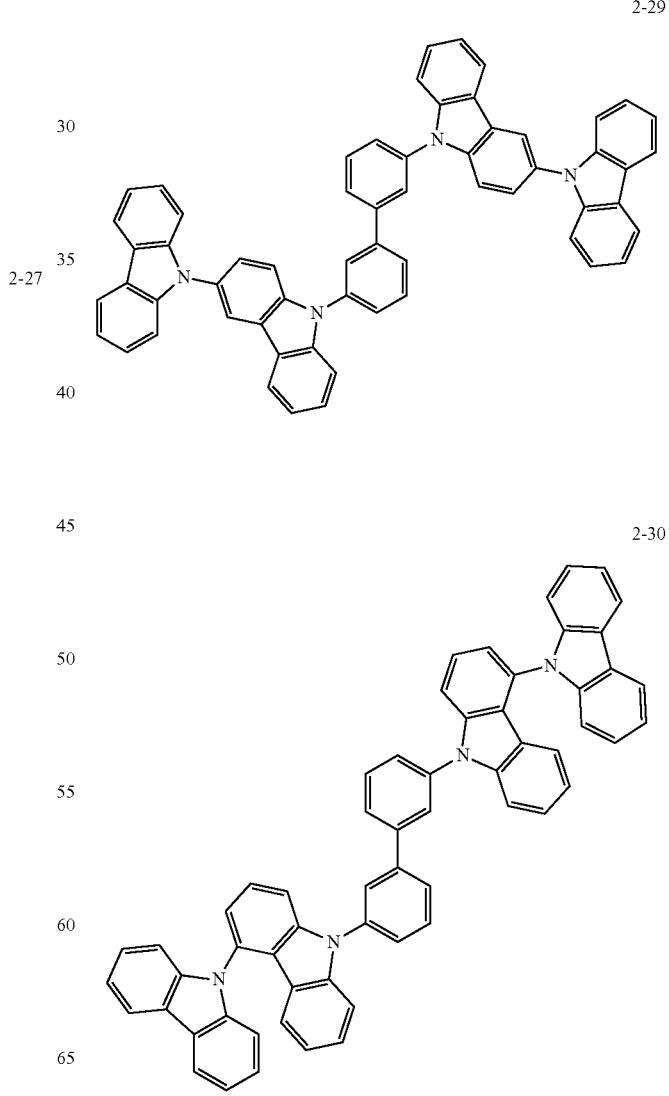

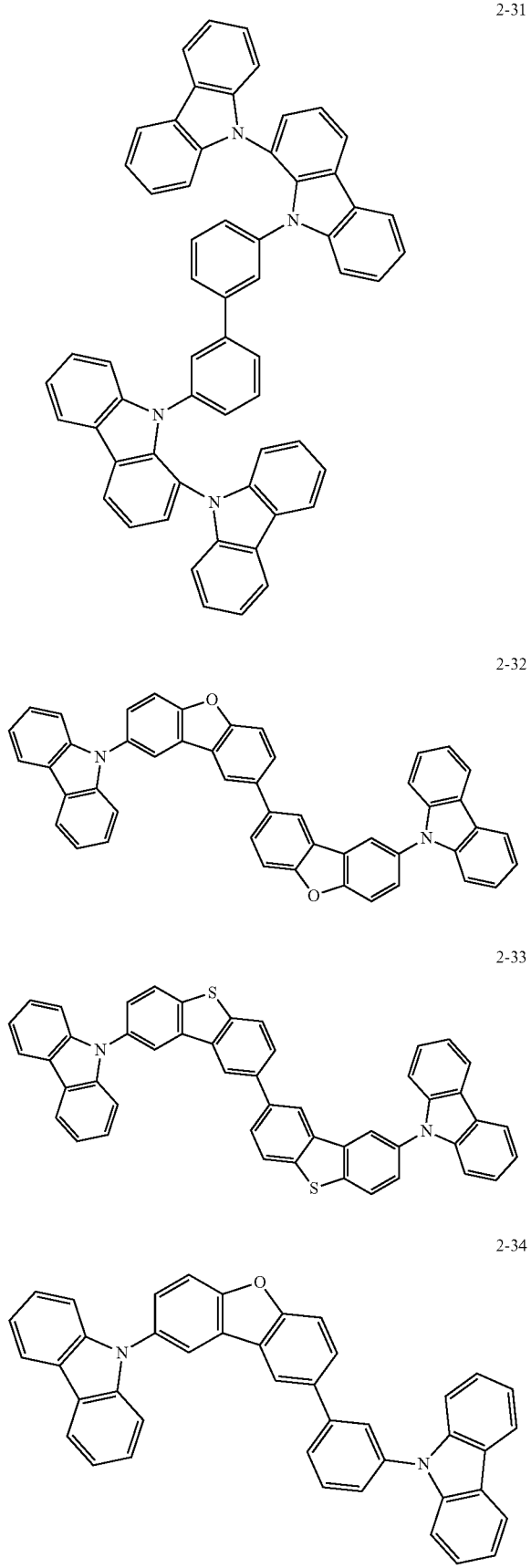

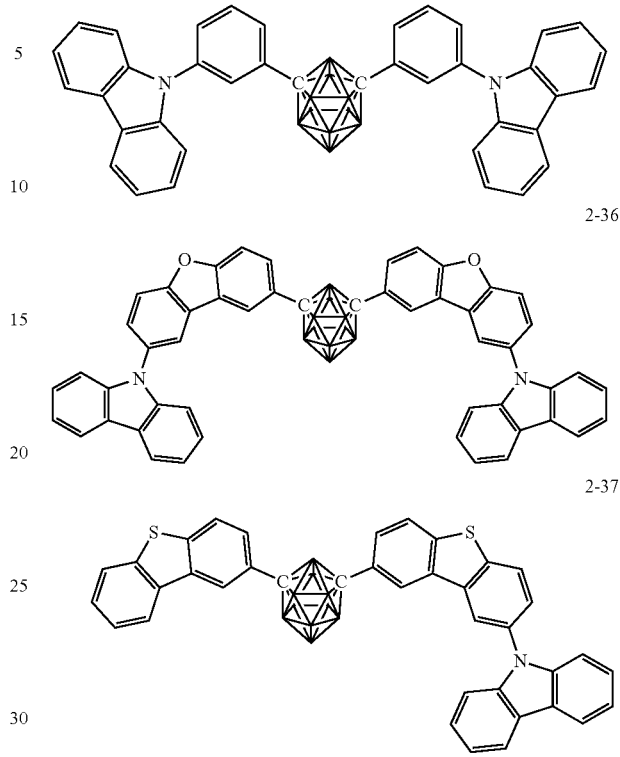

When the light-emitting layer containing a dopant material selected from the thermally activated delayed fluorescent materials each represented by the general formula (1) contains a host material selected from the compounds each represented by the general formula (2), an organic EL device having excellent characteristics can be provided. In addition, the incorporation of two or more kinds of host materials can improve the characteristics. When two kinds of host materials are incorporated, a compound having the larger singlet energy (S1) is preferably incorporated as a second host. When three or more kinds of host materials are incorporated, the materials are referred to as "first host," "second host," "third host," and the like in order of increasing singlet energy.

When two or more kinds of host materials are incorporated, at least one kind thereof is desirably a host material selected from the compounds each represented by the general formula (2). The first host is preferably a compound represented by the general formula (2). The second host only needs to be a compound having a singlet energy (S1) larger than that of the first host, and may be a compound represented by the general formula (2) or may be any other host material. However, the second host is preferably a compound represented by the general formula (2).

Here, the S1 is measured as described below. A sample compound is vapor-deposited onto a quarts substrate by a vacuum deposition method under the condition of a degree of vacuum of $10^{-4}$ Pa or less to form a deposited film having a thickness of 100 nm. The emission spectrum of the deposited film is measured, and a tangent is drawn to the rise-up of the emission spectrum at shorter wavelengths. A wavelength value λedge [nm] of the point of intersection of the tangent and the axis of abscissa is substituted into the following equation (i) to calculate the S1.

$$S1[\text{eV}] = 1{,}239.85/\lambda_{\text{edge}} \tag{i}$$

Next, the structure of the organic EL device of the present invention is described with reference to the drawings. However, the structure of the organic EL device of the present invention is not limited thereto.

FIG. 1 is a sectional view for illustrating a structure example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may include an exciton-blocking layer adjacent to the light-emitting layer, or may include an electron-blocking layer between the light-emitting layer and the hole-injecting layer. The exciton-blocking layer may be inserted on any of the cathode side and the anode side of the light-emitting layer, and may also be inserted simultaneously on both sides. The organic EL device of the present invention includes the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. The hole-injecting/transporting layer means any one or both of the hole-injecting layer and the hole-transporting layer, and the electron-injecting/transporting layer means any one or both of an electron-injecting layer and the electron-transporting layer.

It is possible to adopt a reverse structure as compared to FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated as required.

Substrate

The organic EL device of the present invention is preferably supported by a substrate. The substrate is not particularly limited, and any substrate that has been conventionally used for an organic EL device may be used. For example, a substrate made of glass, a transparent plastic, quartz, or the like may be used.

Anode

A material formed of a metal, an alloy, an electrically conductive compound, or a mixture thereof, which has a large work function (4 eV or more), is preferably used as an anode material in the organic EL device. Specific examples of such electrode material include metals, such as Au, and conductive transparent materials, such as CuI, indium tin oxide (ITO), $SnO_2$, and ZnO. Further, it may be possible to use an amorphous material, such as IDIXO ($In_2O_3$—ZnO), which may be used for manufacturing a transparent conductive film. In order to produce the anode, it may be possible to form any of those electrode materials into a thin film by using a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode materials is subjected to vapor deposition or sputtering. Alternatively, when a coatable substance, such as an organic conductive compound, is used, it is also possible to use a wet film-forming method, such as a printing method or a coating method. When luminescence is taken out from the anode side, the transmittance of the anode is desirably controlled to more than 10%. Further, the sheet resistance as the anode is preferably several hundred $\Omega/\square$ or less. The thickness of the film is, depending on its material, selected from usually the range of from 10 nm to 1,000 nm, preferably the range of from 10 nm to 200 nm.

Cathode

Meanwhile, a material formed of a metal (referred to as electron-injecting metal), an alloy, an electrically conductive compound, or a mixture thereof, which has a small work function (4 eV or less), is used as a cathode material. Specific examples of such electrode material include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than that of the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of an electron-injecting property and durability against oxidation or the like. The cathode may be produced by forming any of those cathode materials into a thin film by using a method such as vapor deposition or sputtering. Further, the sheet resistance as the cathode is preferably several hundred $\Omega/\square$ or less, and the thickness of the film is selected from usually the range of from 10 nm to 5 μm, preferably the range of from 50 nm to 200 nm. Any one of the anode and cathode of the organic EL device is preferably transparent or semi-transparent because emitted light is transmitted therethrough and the light emission luminance improves.

Further, after any of the above-mentioned metals is formed into a film having a thickness of from 1 nm to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and the cathode have transparency.

Light-Emitting Layer

The light-emitting layer is a layer that emits light after the production of an exciton by the recombination of a hole injected from the anode and an electron injected from the cathode. In the light-emitting layer, the TADF material of the present invention may be used alone, or the TADF material of the present invention may be used together with a host material. When the TADF material of the present invention is used together with the host material, the TADF material serves as an organic light-emitting dopant material.

Only one kind of organic light-emitting dopant material may be incorporated into the light-emitting layer, or two or more kinds of organic light-emitting dopant materials may be incorporated thereinto. The content of the organic light-emitting dopant material is preferably from 0.1 wt % to 50 wt %, more preferably from 1 wt % to 30 wt % with respect to the host material.

In order to improve the probability of recombining a hole and an electron in the light-emitting layer, the IP of the organic light-emitting dopant material is preferably made smaller than the IP of the host material.

The measurement of an IP can be performed under air with a photoelectron spectrometer. Specifically, the IP is measured by: irradiating a material with light; and measuring the amount of electrons produced by charge separation at that time. An apparatus for the measurement is, for example, a photoelectron spectrometer (AC-3) manufactured by Riken Keiki Co., Ltd.

The organic light-emitting dopant material in the light-emitting layer preferably has an emission maximum wavelength in the range of from 440 nm to 470 nm, and more preferably has the emission maximum wavelength in the range of from 450 nm to 470 nm.

Although a known host material to be used in a phosphorescent light-emitting device or a fluorescent light-emitting device can be used as the host material in the light-emitting layer, a compound represented by the general formula (2) is preferably used. In addition, a plurality of kinds of host materials may be used in combination. When the plurality of kinds of host materials are used in combination, at least one kind of host material is preferably selected from the compounds each represented by the general formula (2).

The known host material that can be used is a compound having a hole-transporting ability or an electron-transporting ability, and having a high glass transition temperature, and preferably has a S1 larger than that of the light-emitting dopant material.

Such other host material is made public by many patent literatures and the like, and hence can be selected from the literatures and the like. The host material is not particularly limited, and specific examples thereof include an indole derivative, a carbazole derivative, an indolocarbazole derivative, a traizole derivative, an oxazole derivative, an oxadiazole derivative, an imidazole derivative, a phenylenediamine derivative, an arylamine derivative, a styrylanthracene derivative, a fluorenone derivative, a stilbene derivative, a carborane compound, a porphyrin-based compound, a phthalocyanine derivative, various metal complexes typified by a metal complex of an 8-quinolinol derivative, metal phthalocyanine, and a metal complex of a benzoxazole or benzothiazole derivative, and polymer compounds, such as a poly (N-vinylcarbazole) derivative, an aniline-based copolymer, a thiophene oligomer, a polythiophene derivative, a polyphenylene derivative, a polyphenylene vinylene derivative, and a polyfluorene derivative.

When a plurality of kinds of host materials are used, the respective hosts can be vapor-deposited from different deposition sources, or the plurality of kinds of hosts can be simultaneously vapor-deposited from one deposition source by preliminarily mixing the hosts before the vapor deposition to provide a preliminary mixture.

Injecting Layer

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

Hole-Blocking Layer

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole in the light-emitting layer by blocking holes while transporting electrons.

A known hole-blocking layer material can also be used for the hole-blocking layer.

Electron-Blocking Layer

The electron-blocking layer has, in a broad sense, the function of a hole-transporting layer, and is capable of improving the probability of re combining an electron and a hole in the light-emitting layer by blocking electrons while transporting holes.

A known material for an electron-blocking layer may be used as a material for the electron-blocking layer, and a material for the hole-transporting layer to be described later may be used as required. The thickness of the electron-blocking layer is preferably from 3 nm to 100 nm, more preferably from 5 nm to 30 nm.

Exciton-Blocking Layer

The exciton-blocking layer refers to a layer for blocking excitons produced by the recombination of a hole and an electron in the light-emitting layer from diffusing into charge-transporting layers. The insertion of this layer enables efficient confinement of the excitons in the light-emitting layer, thereby being able to improve the luminous efficiency of the device. In a device in which two or more light-emitting layers are adjacent to each other, the exciton-blocking layer can be inserted between two adjacent light-emitting layers.

A known material for an exciton-blocking layer may be used as a material for the exciton-blocking layer. Examples thereof include 1,3-dicarbazolylbenzene (mCP) and bis(2-methyl-8-quinolinolato)-4-phenylphenolatoaluminum(III) (BAlq).

Hole-Transporting Layer

The hole-transporting layer is formed of a hole-transporting material having a function of transporting holes, and a single hole-transporting layer or a plurality of hole-transporting layers may be formed.

The hole-transporting material has a hole-injecting property or a hole-transporting property or has an electron-blocking property, and any of an organic material and an inorganic material may be used as the hole-transporting material. Any compound selected from conventionally known compounds may be used for the hole-transporting layer. Examples of such hole-transporting material include a porphyrin derivative, an arylamine derivative, a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. Of those, a porphyrin derivative, an arylamine derivative, or a styrylamine derivative is preferably used, and an arylamine compound is more preferably used.

Electron-Transporting Layer

The electron-transporting layer is formed of a material having a function of transporting electrons, and a single electron-transporting layer or a plurality of electron-transporting layers may be formed.

An electron-transporting material (which also serves as a hole-blocking material in some cases) only needs to have a function of transferring electrons injected from the cathode into the light-emitting layer. Any compound selected from conventionally known compounds may be used for the electron-transporting layer. Examples thereof include a polycyclic aromatic derivative, such as naphthalene, anthracene, or phenanthroline, a tris(8-quinolinolato)aluminum (III) derivative, a phosphine oxide derivative, a nitro-substituted fluorene derivative, a diphenylquinone derivative, a thiopyran dioxide derivative, a carbodiimide, a fluorenylidenemethane derivative, anthraquinodimethane and anthrone derivatives, a bipyridine derivative, a quinoline derivative, an oxadizole derivative, a benzimidazole derivative, a benzothiazole derivative, and an indolocarbazole derivative. Further, it is also possible to use a polymer material in which any of those materials is introduced in a polymer chain or is used as a polymer main chain.

A method of producing each layer at the time of the production of the organic EL device of the present invention is not particularly limited, and the layer may be produced by any one of a dry process and a wet process.

EXAMPLES

The present invention is hereinafter described in more detail by way of Examples. However, the present invention is not limited to Examples below.

Compounds used in Examples are shown below. Compounds 1-17, 1-24, 1-36, 2-4, 2-12, 2-15, 2-20, and 2-37 are compounds listed in the foregoing.

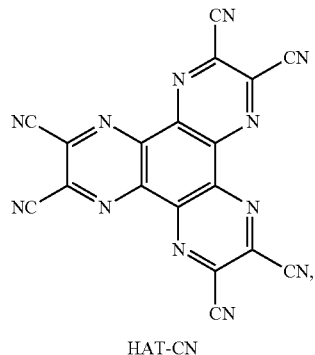

HAT-CN

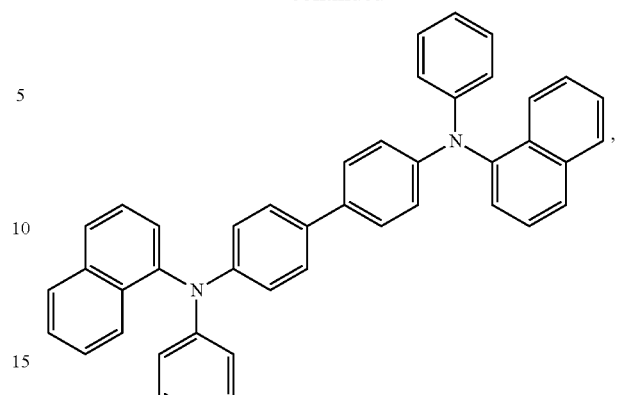

NPD

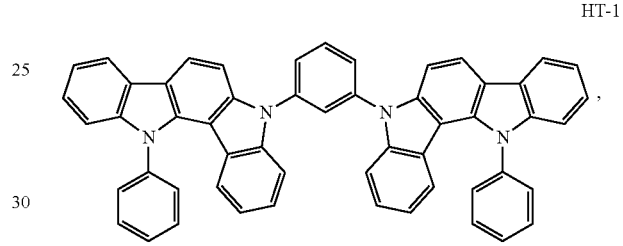

HT-1

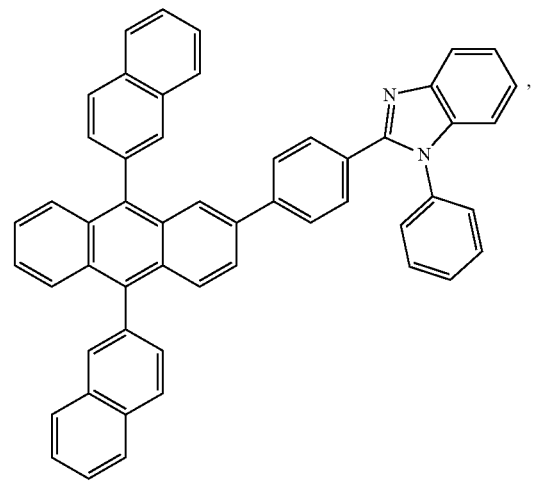

ET-1

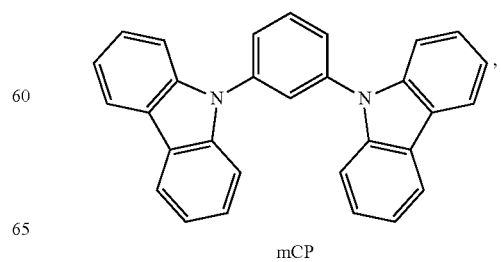

mCP

-continued

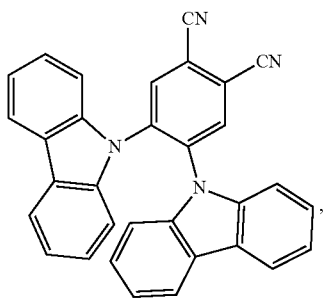

TD-2

TD-3

Synthesis Example 1

TD-1

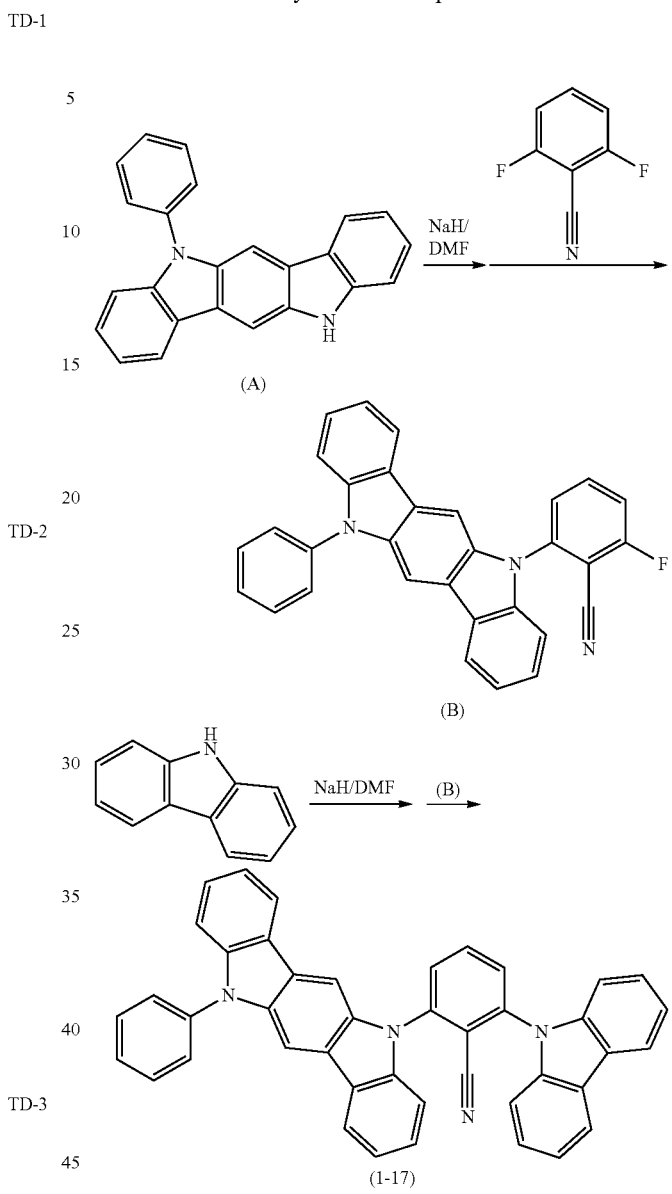

Under a nitrogen atmosphere, 0.95 g of NaH and 10 ml of DMF were added and stirred at room temperature. Then, 7.13 g of an intermediate (A) dissolved in 100 ml of DMF was added to the mixture, and the whole was stirred at room temperature for 30 min. Further, 6.58 g of 2,6-difluorobenzonitrile was added to the resultant, and the mixture was stirred at room temperature for 6 hr. 500 ml of water was added to the reaction solution, and the mixture was stirred at room temperature for 1 hr, followed by the separation of a precipitated solid by filtration. The resultant solid was purified by silica gel column chromatography to provide 7.81 g of an intermediate (B) (yield: 80%).

Under a nitrogen atmosphere, 1.00 g of NaH and 10 ml of DMF were added and stirred at room temperature. Then, 3.47 g of carbazole dissolved in 100 ml of DMF was added to the mixture, and the whole was stirred at room temperature for 30 min. Further, 7.81 g of the intermediate (B) was added to the resultant, and the mixture was stirred at room temperature for 1 hr. 200 ml of water was added to the reaction solution, and the mixture was stirred at room temperature for 1 hr, followed by the separation of a precipitated solid by filtration. The resultant solid was purified by silica gel column chromatography and recrystallization to provide 8.16 g of Compound (1-17) as a yellow solid (yield: 79%).

Figure 2:
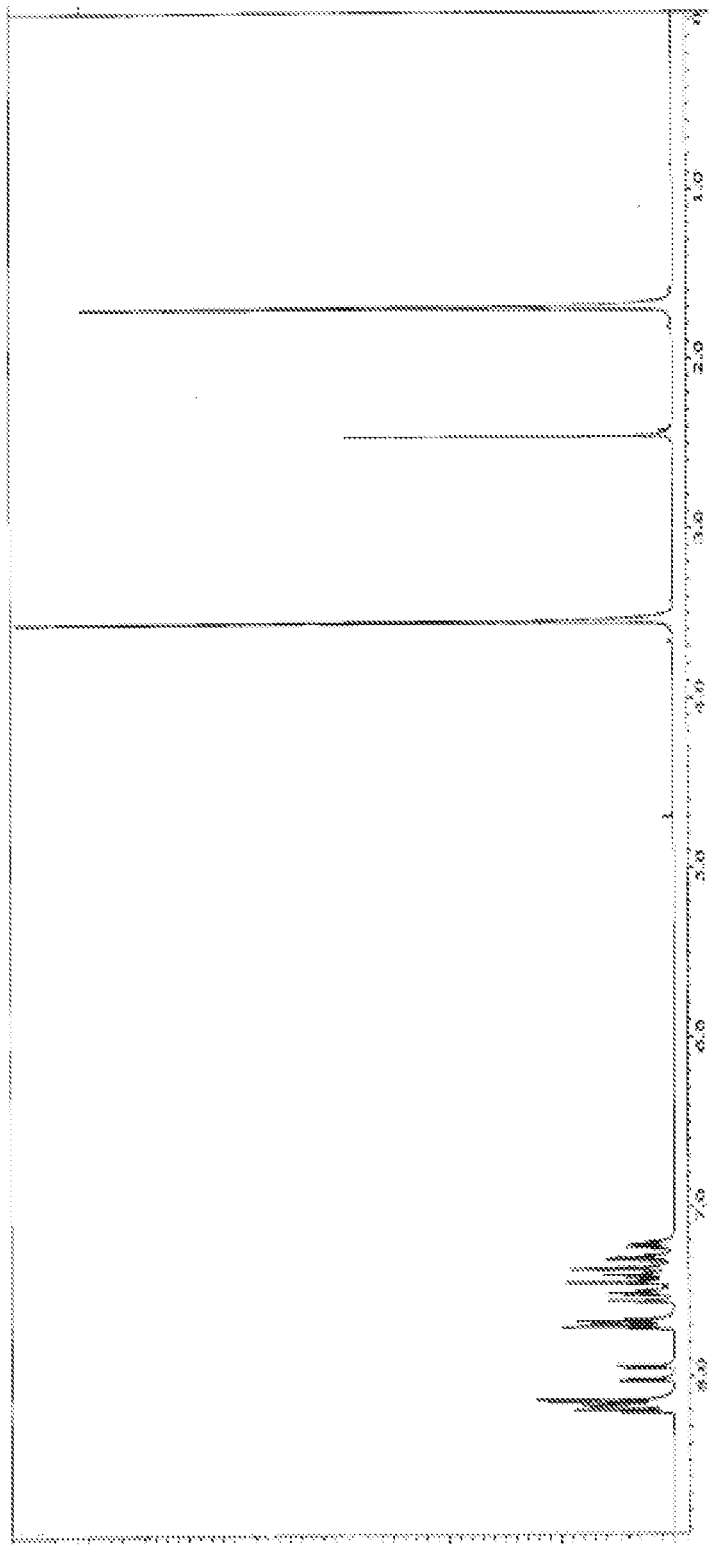
FIG. 2 is a 1H-NMR chart of a thermally activated delayed fluorescent material.

APCI-TOFMS found that the compound had a [M+1] peak at an m/z of 599. The results of the 1H-NMR measurement (measurement solvent: THF-d8) of the compound are shown in FIG. 2.

Synthesis Example 2

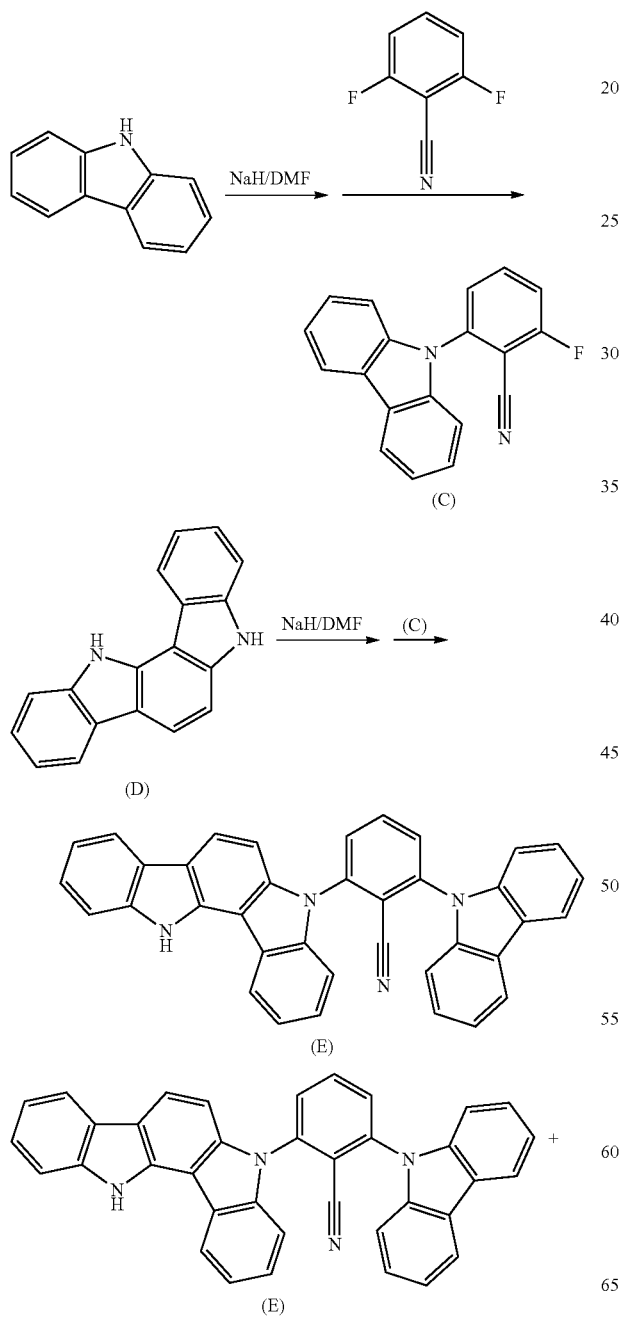

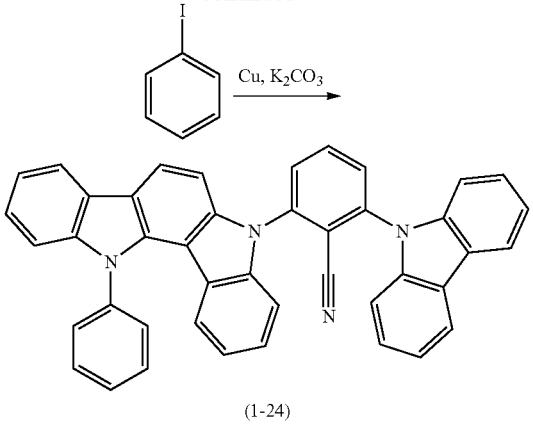

(1-24)

Under a nitrogen atmosphere, 3.44 g of NaH and 10 ml of DMF were added and stirred at room temperature. Then, 11.90 g of carbazole dissolved in 50 ml of DMF was added to the mixture, and the whole was stirred at room temperature for 30 min. Further, 19.81 g of 2,6-difluorobenzonitrile was added to the resultant, and the mixture was stirred at room temperature for 3 hr. 200 ml of water was added to the reaction solution, and the mixture was stirred at room temperature for 1 hr, followed by the separation of a precipitated solid by filtration. The resultant solid was purified by silica gel column chromatography and recrystallization to provide 12.76 g of an intermediate (C) (yield: 62%).

Under a nitrogen atmosphere, 4.30 g of NaH and 10 ml of DMF were added and stirred at room temperature. Then, 12.59 g of an intermediate (D) dissolved in 50 ml of DMF was added to the mixture, and the whole was stirred at room temperature for 30 min. Further, 12.76 g of an intermediate (C) dissolved in 50 ml of DMF was added to the resultant, and the mixture was stirred at room temperature for 1 hr. 200 ml of water was added to the reaction solution, and the mixture was stirred at room temperature for 1 hr, followed by the separation of a precipitated solid by filtration. The resultant solid was purified by recrystallization to provide 22.11 g of an intermediate (E) (yield: 85%).

Under a nitrogen atmosphere, 22.11 g of the intermediate (E), 495.53 g of iodobenzene, 64.31 g of potassium carbonate, and 17.47 g of copper were added and stirred at 180° C. The solvent was removed by distillation under reduced pressure, and the resultant solid was purified by recrystallization to provide 16.42 g of Compound (1-24) as a white solid (yield: 65%).

Figure 3:
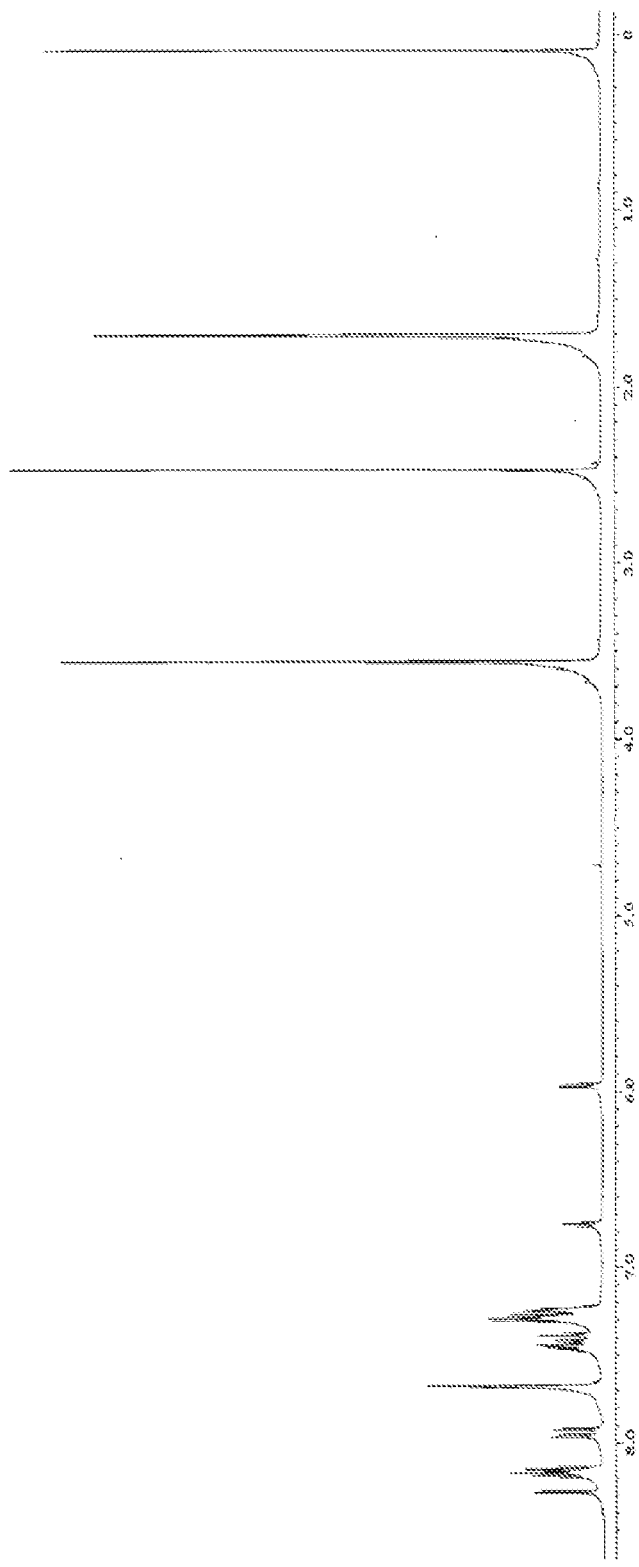
FIG. 3 is a 1H-NMR chart of a thermally activated delayed fluorescent material.

APCI-TOFMS found that the compound had a [M+1] peak at an m/z of 599. The results of the 1H-NMRmeasurement (measurement solvent: THF-d8) of the compound are shown in FIG. 3.

Synthesis Example 3

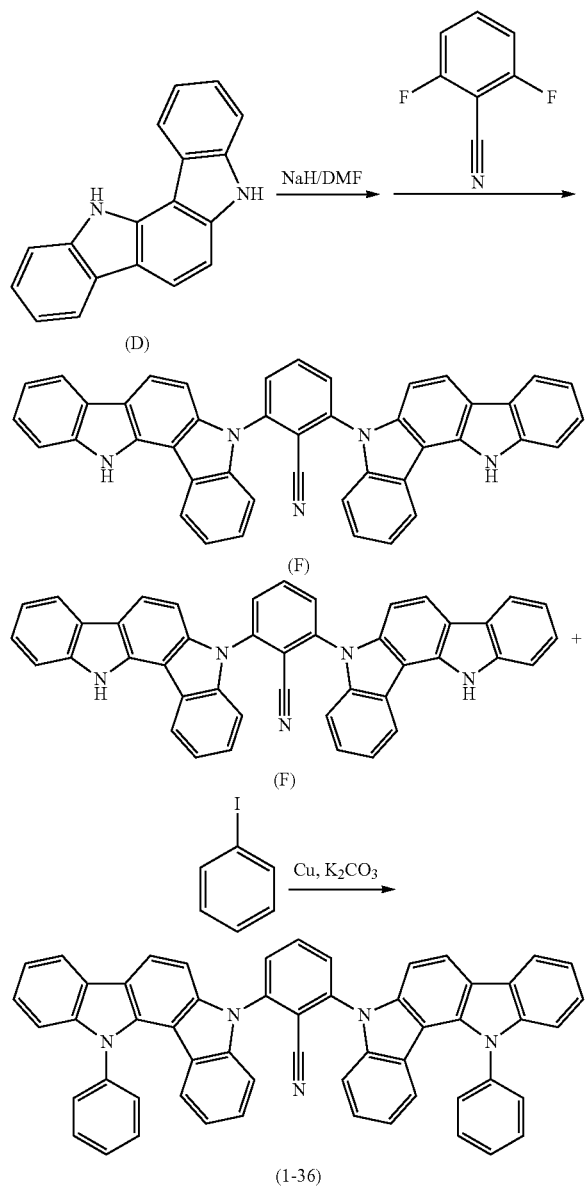

Under a nitrogen atmosphere, 6.94 g of NaH and 100 ml of DMF were added and stirred at room temperature. Then, 20.00 g of an intermediate (D) dissolved in 100 ml of DMF was added to the mixture, and the whole was stirred at room temperature for 20 min. Further, 5.43 g of 2,6-difluorobenzonitrile was added to the resultant, and the mixture was stirred at 50° C. for 8 hr. 200 ml of water was added to the reaction solution, and the mixture was stirred at room temperature for 1 hr, followed by the separation of a precipitated solid by filtration. The resultant solid was purified by recrystallization to provide 21.31 g of an intermediate (F) (yield: 88%).

Under a nitrogen atmosphere, 15.00 g of the intermediate (F), 599.79 g of iodobenzene, 37.25 g of potassium carbonate, and 10.10 g of copper were added and stirred at 180° C. The solvent was removed by distillation under reduced pressure, and the resultant solid was purified by column chromatography and recrystallization to provide 15.25 g of Compound (1-36) as a yellow solid (yield: 81%).

Figure 4:
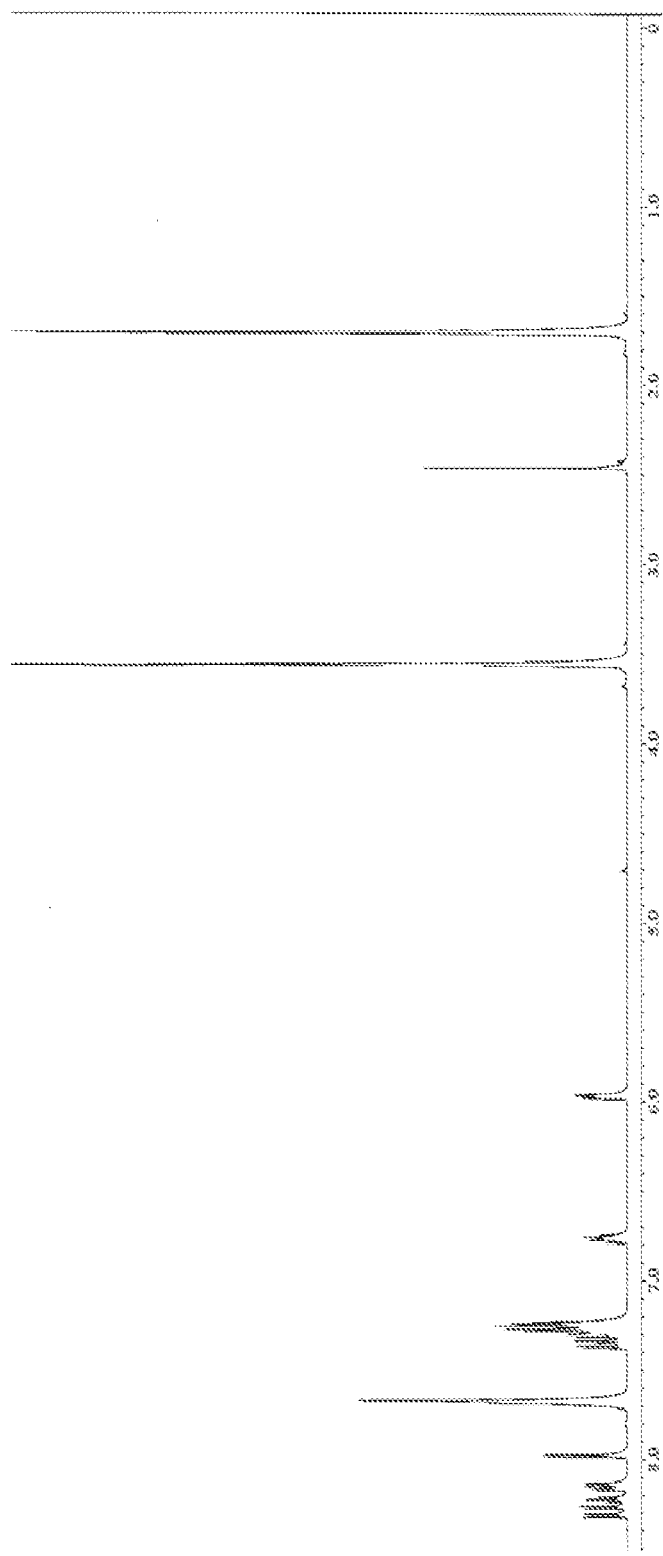
FIG. 4 is a 1H-NMR chart of a thermally activated delayed fluorescent material.

APCI-TOFMS found that the compound had a [M+1] peak at an m/z of 764. The results of the 1H-NMR measurement (measurement solvent: THF-d8) of the compound are shown in FIG. 4.

The S1 and IP of each of Compounds 1-17, 1-24, 1-36, 2-4, 2-12, 2-15, 2-20, and 2-37, and mCP, TD-1, TD-2, and TD-3 shown in the foregoing were measured. A measurement method and a calculation method are the methods described in the foregoing.

TABLE 1

| Compound | S1 [eV] | IP [eV] |
|---|---|---|
| 1-17 | 2.9 | 5.7 |
| 1-24 | 3.0 | 5.8 |
| 1-36 | 2.9 | 5.8 |
| 2-4 | 3.6 | 6.2 |
| 2-12 | 3.5 | 6.5 |
| 2-15 | 3.4 | 5.9 |
| 2-20 | 3.5 | 6.0 |
| 2-37 | 3.4 | 6.3 |
| mCP | 3.7 | 6.1 |
| TD-1 | 2.8 | 6.3 |
| TD-2 | 2.8 | 5.8 |
| TD-3 | 2.1 | 5.8 |

Experiment Example 1

Figure 5:
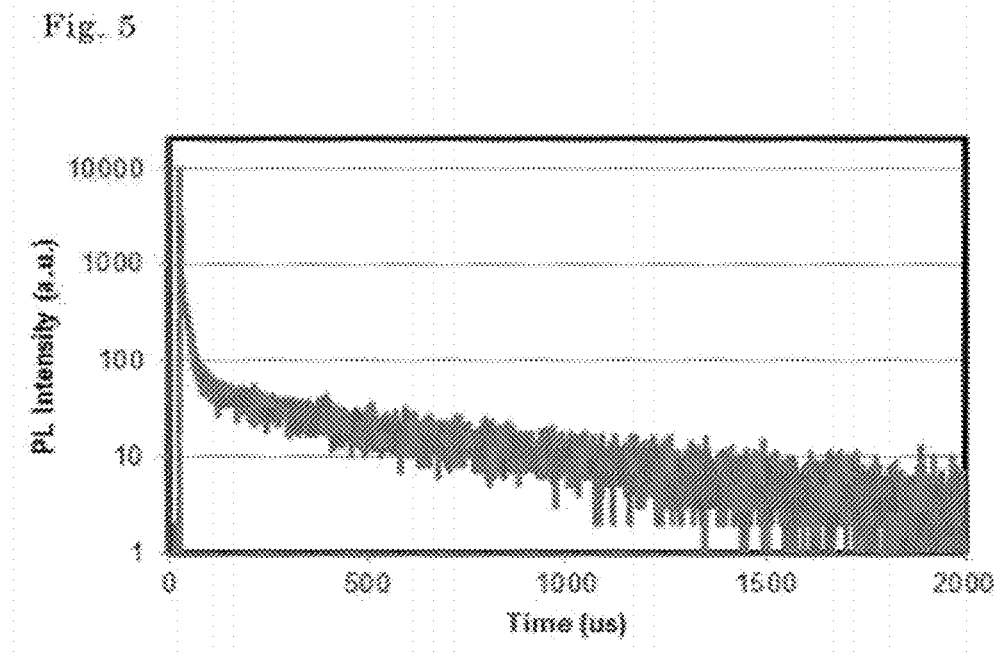
FIG. 5 is a time-resolved spectrum of a thermally activated delayed fluorescent material.
Figure 6:
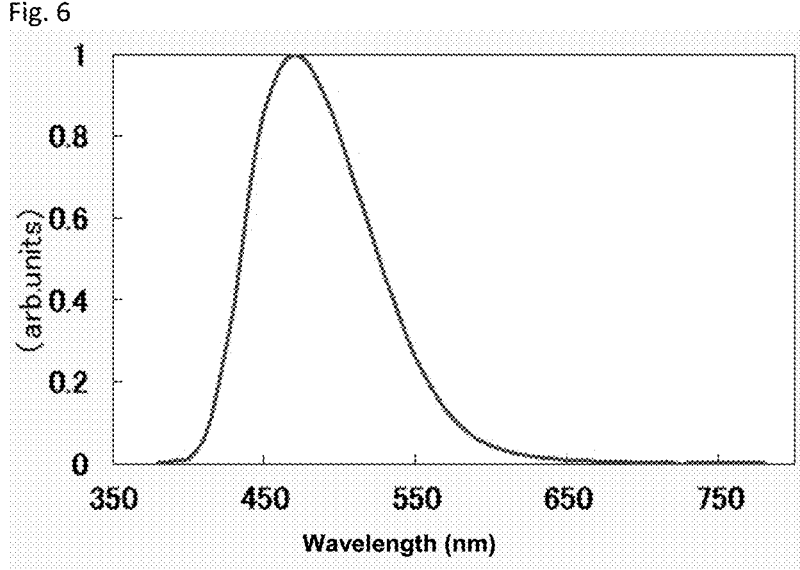
FIG. 6 is an emission spectrum of an organic EL device of the present invention.

The fluorescence lifetime and quantum yield of Compound 1-17 were measured. Compound (1-17) and Compound (2-4) were vapor-deposited from different deposition sources onto a quartz substrate by a vacuum deposition method under the condition of a degree of vacuum of $10^{-4}$ Pa or less to form a co-deposited film having a thickness of 100 nm in which the concentration of Compound 1-17 was 5.0 wt %. The emission spectrum of the thin film was measured and light emission having a peak at 469 nm was observed. In addition, measurement was performed with a small fluorescence lifetime-measuring apparatus (Quantaurus-tau manufactured by Hamamatsu Photonics K.K.) under air and under a nitrogen atmosphere to provide a transient decay curve shown in FIG. 5. Under air, fluorescence having an excitation lifetime of 9.1 ns was observed, and under the nitrogen atmosphere, fluorescence having an excitation lifetime of 9.1 ns and delayed fluorescence having an excitation lifetime of 478.9 μs were observed. Further, the photoluminescence quantum efficiencies of the thin film were measured with an absolute PL quantum yield-measuring apparatus (Quantaurus-QY manufactured by Hamamatsu Photonics K.K.) under air and under the nitrogen atmosphere at an excitation wavelength of 300 nm. As a result, the photoluminescence quantum efficiency under air was 44%, and the photoluminescence quantum efficiency under the nitrogen atmosphere was 50%.

The fluorescence lifetimes and quantum yields of Compounds 1-24 and 1-36 were also each measured in the same manner as in Experiment Example 1. As a result, delayed fluorescence was observed.

Example 1

Each thin film was laminated on a glass substrate having formed thereon an anode formed of ITO having a thickness of 70 nm by a vacuum deposition method at a degree of vacuum of $4 \times 10^{-5}$ Pa. First, HAT-CN serving as a hole-injecting layer was formed on ITO so as to have a thickness of 10 nm, and then NPD serving as a hole-transporting layer was formed so as to have a thickness of 25 nm. Next, HT-1 serving as an electron-blocking layer was formed so as to have a thickness of 5 nm. Then, Compound (2-12) serving as a host and Compound (1-17) serving as a dopant were respectively co-deposited from different deposition sources to form a light-emitting layer having a thickness of 30 nm. At this time, the co-deposition was performed under such a deposition condition that the concentration of Compound (1-17) became 15 wt %. Next, Compound (2-12) serving as a hole-blocking layer was formed so as to have a thickness of 5 nm. Next, ET-1 serving as an electron-transporting layer was formed so as to have a thickness of 40 nm. Further, lithium fluoride (LiF) serving as an electron-injecting layer was formed on the electron-transporting layer so as to have a thickness of 1 nm. Finally, aluminum (Al) serving as a cathode was formed on the electron-injecting layer so as to have a thickness of 70 nm. Thus, an organic EL device was produced.

Examples 2 to 6 and Comparative Examples 1 to 3

Organic EL devices were each produced in the same manner as in Example 1 except that the host and the dopant were changed to compounds shown in Table 2.

Example 7

Each thin film was laminated on a glass substrate having formed thereon an anode formed of ITO having a thickness of 70 nm by a vacuum deposition method at a degree of vacuum of $4.0 \times 10^{-5}$ Pa. First, HAT-CM serving as a hole-injecting layer was formed on ITO so as to have a thickness of 10 nm, and then NPD serving as a hole-transporting layer was formed so as to have a thickness of 25 nm. Next, HT-1 serving as an electron-blocking layer was formed so as to have a thickness of 5 nm. Next, Compound (2-15) serving as a host, Compound (2-4) serving as a second host, and Compound (1-17) serving as a dopant were respectively co-deposited from different deposition sources to form a light-emitting layer having a thickness of 30 nm. At this time, the co-deposition was performed under such a deposition condition that the concentration of Compound (1-17) became 15 wt. % and the weight ratio between the host and the second host became 50:50. Next, Compound (2-12) serving as a hole-blocking layer was formed so as to have a thickness of 5 nm. Next, ET-1 serving as an electron-transporting layer was formed so as to have a thickness of 40 nm. Further, lithium fluoride (LiF) serving as an electron-injecting layer was formed on the electron-transporting layer so as to have a thickness of 1 nm. Finally, aluminum (Al) serving as a cathode was formed on the electron-injecting layer so as to have a thickness of 70 nm. Thus, an organic EL device was produced.

The compounds used as the dopants, the hosts, and the second host are shown in Table 2.

TABLE 2

| | Dopant | Host | Second host |
|---|---|---|---|
| Example 1 | 1-17 | 2-12 | — |
| Example 2 | 1-17 | 2-4 | — |
| Example 3 | 1-17 | 2-15 | — |
| Example 4 | 1-17 | mCP | — |
| Example 5 | 1-24 | 2-20 | — |
| Example 6 | 1-36 | 2-37 | — |

TABLE 2-continued

| | Dopant | Host | Second host |
|---|---|---|---|
| Example 7 | 1-17 | 2-15 | 2-4 |
| Comparative Example 1 | TD-1 | 2-12 | — |
| Comparative Example 2 | TD-2 | 2-12 | — |
| Comparative Example 3 | TD-3 | 2-12 | — |

The maximum wavelengths of the emission spectra of the produced organic EL devices, and the luminances, driving voltages, luminous efficiencies, and lifetimes of the devices are shown in Table 3. The maximum wavelengths, the luminances, the driving voltages, and the luminous efficiencies are values at a driving current density of 2.5 mA/cm$^2$, and are initial characteristics. The lifetimes were each obtained by measuring a time period required for a luminance to attenuate from an initial luminance of 500 cd/m$^2$ to 95% of the initial luminance.

TABLE 3

| | Maximum emission wavelength (nm) | Luminance (cd/m$^2$) | Driving voltage (V) | Luminous efficiency (lm/W) | Lifetime (h) |
|---|---|---|---|---|---|
| Example 1 | 470 | 133 | 6.2 | 2.7 | 76 |
| Example 2 | 470 | 152 | 6.0 | 3.2 | 66 |
| Example 3 | 465 | 145 | 5.2 | 3.5 | 80 |
| Example 4 | 470 | 127 | 6.4 | 2.4 | 40 |
| Example 5 | 450 | 124 | 5.9 | 2.6 | 78 |
| Example 6 | 470 | 164 | 6.0 | 3.4 | 90 |
| Example 7 | 470 | 155 | 5.5 | 3.5 | 104 |
| Comparative Example 1 | 495 | 51 | 6.5 | 1.0 | 29 |
| Comparative Example 2 | 530 | 283 | 6.0 | 4.9 | 37 |
| Comparative Example 3 | 630 | 36 | 5.0 | 0.9 | 22 |

As can be seen from Table 3, an organic EL device using a TADF material represented by the general formula (1) as a light-emitting dopant has a lower driving voltage, shows more satisfactory luminous efficiency, and has a more excellent lifetime characteristic as compared to the case where TD-1 serving as a known TADF material is used. Further, as can be seen from the table, the organic EL device has a shorter emission wavelength and hence has a more excellent color purity as compared to the case where any one of the indolocarbazole compound-based materials TD-2 and TD-3 serving as known TADF materials is used.

INDUSTRIAL APPLICABILITY

The organic EL device of the present invention has a low driving voltage, high luminous efficiency, and a long lifetime, and hence there is a possibility that the device can be utilized in a portable equipment display, and can also be utilized in the organic EL display of a television or the like, or in organic EL lighting.

REFERENCE SIGNS LIST

1 substrate, 2 anode, 3 hole-injecting layer, 4 hole-transporting layer, 5 light-emitting layer, 6 electron-transporting layer, 7 cathode

The invention claimed is:

1. An organic electroluminescent device, comprising one or more light-emitting layers between an anode and a cathode opposite to each other, wherein at least one of the light-emitting layers contains a thermally activated delayed fluorescent material represented by the following general formula (1) as a light-emitting dopant:

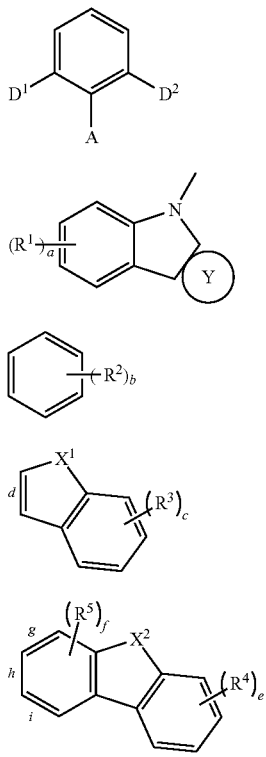

where $D^1$ and $D^2$ each independently represent a nitrogen-containing heterocycle represented by the formula (1a), a ring Y in the formula (1a) of one of $D^1$ or $D^2$ is represented by formula (1 a-1), and the ring Y in the formula (1a) of the other of $D^1$ or $D^2$ is represented by the formula (1 a-2) or (1 a-3), and when the ring Y is represented by the formula (1 a-2), the ring Y is fused at a position d, and when the ring Y is represented by the formula (1a-3), the ring Y is fused at a position g, h, or i, $X^1$ and $X^2$ each independently represent O, S, or N—$R^6$, $R^1$ to $R^6$ each independently represent an aliphatic hydrocarbon group having 1 to 8 carbon atoms, an aromatic hydrocarbon group having 6 to 10 carbon atoms, or an aromatic heterocyclic group having 3 to 12 carbon atoms, A represents a cyano group, a, b, c, and e each independently represent an integer of from 0 to 4, and f represents an integer of from 0 to 2.

2. An organic electroluminescent device according to claim 1, wherein the ring Y in the formula (1a) of the other of $D^1$ or $D^2$ is represented by the formula (1a-3).

3. An organic electroluminescent device according to claim 2, wherein $X^2$ in the formula (1a-3) represents N—$R^6$.

4. An organic electroluminescent device according to any one of claims 1, 2 and 3, wherein the light-emitting layer containing the thermally activated delayed fluorescent material contains a host material.

5. An organic electroluminescent device according to claim 4, wherein the host material comprises a compound represented by the following general formula (2):

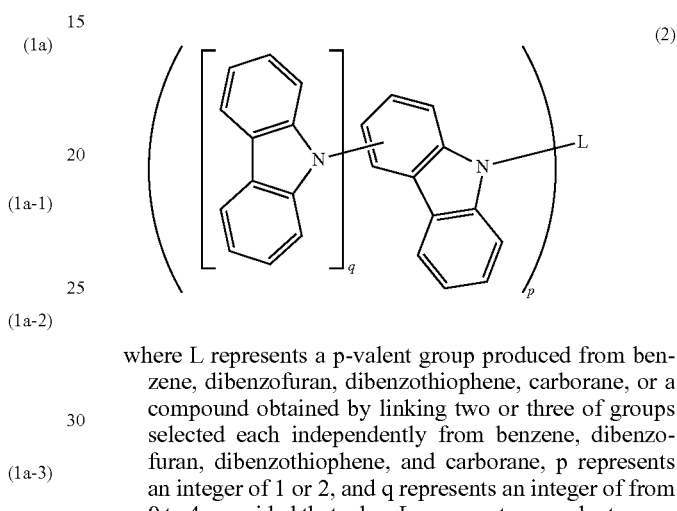

where L represents a p-valent group produced from benzene, dibenzofuran, dibenzothiophene, carborane, or a compound obtained by linking two or three of groups selected each independently from benzene, dibenzofuran, dibenzothiophene, and carborane, p represents an integer of 1 or 2, and q represents an integer of from 0 to 4, provided that when L represents a p-valent group produced from a single benzene, q represents an integer of from 1 to 4.

6. An organic electroluminescent device according to claim 5, wherein the host material includes a first host and a second host selected from compounds each having a singlet excitation energy (S 1) larger than that of the first host, and at least one of the first host or the second host comprises a compound represented by the general formula (2).

7. An organic electroluminescent device according to claim 5, wherein the light-emitting layer contains at least two kinds of host materials each represented by the general formula (2).

8. An organic electroluminescent device according to claim 4, wherein an ionization potential of the thermally activated delayed fluorescent material is smaller than an ionization potential of the host material.

9. An organic electroluminescent device according to claim 1, wherein the thermally activated delayed fluorescent material has an emission maximum wavelength in a range of from 440 nm to 470 nm.

* * * * *